United States Patent
Chua et al.

(10) Patent No.: US 9,232,915 B2
(45) Date of Patent: Jan. 12, 2016

(54) METHOD AND APPARATUS FOR DERIVING A HEALTH INDEX FOR DETERMINING CARDIOVASCULAR HEALTH

(75) Inventors: Juliana Chua, Singapore (SG); Myo Myint Aung, Singapore (SG); Xinying Cheah, Singapore (SG); Visit Thaveeprungsriporn, Singapore (SG)

(73) Assignee: NITTO DENKO CORPORATION, Osaka (JP)

( * ) Notice: Subject to any disclaimer, the term of this patent is extended or adjusted under 35 U.S.C. 154(b) by 126 days.

(21) Appl. No.: 13/991,422

(22) PCT Filed: Dec. 1, 2011

(86) PCT No.: PCT/SG2011/000424
§ 371 (c)(1),
(2), (4) Date: Jun. 3, 2013

(87) PCT Pub. No.: WO2012/099534
PCT Pub. Date: Jul. 26, 2012

(65) Prior Publication Data
US 2013/0289366 A1     Oct. 31, 2013

Related U.S. Application Data

(63) Continuation of application No. 13/010,705, filed on Jan. 20, 2011, now Pat. No. 8,761,853.

(60) Provisional application No. 61/490,331, filed on May 26, 2011.

(51) Int. Cl.
*G06F 19/00* (2011.01)
*A61B 5/00* (2006.01)
(Continued)

(52) U.S. Cl.
CPC .......... *A61B 5/14552* (2013.01); *A61B 5/0205* (2013.01); *A61B 5/02028* (2013.01); *A61B 5/02416* (2013.01); *A61B 5/14551* (2013.01);
(Continued)

(58) Field of Classification Search
None
See application file for complete search history.

(56) References Cited

U.S. PATENT DOCUMENTS 7,635,337 B2    12/2009  Huiku et al.
8,478,389 B1 *  7/2013   Brockway et al. ............ 600/509
(Continued)

FOREIGN PATENT DOCUMENTS

WO    2009063446 A2    5/2009
WO    2010078226 A1    7/2010

OTHER PUBLICATIONS

West JB, Control of Breathing, Respiratory Physiology, 2012, pp. 130-132.
(Continued)

*Primary Examiner* — William Thomson
*Assistant Examiner* — Davin K Sands
(74) *Attorney, Agent, or Firm* — InnovationCapital Law Group; Vic Lin

(57) ABSTRACT

A method 1300 and apparatus for deriving a health index for determining cardiovascular health of a person is disclosed herein. In a described embodiment, the method 1300 includes (i) obtaining values of respiratory rate, Sp02 and heart rate from a PPG signal of the person at step 1304; (ii) assigning a score based on the values from a reference scoring system at step 1306; and (iii) deriving the health index based on the assigned scores at step 1308/1314. A method and device for obtaining the PPG signal at optimum pressure is also disclosed.

20 Claims, 41 Drawing Sheets

(51) Int. Cl.
  *A61B 5/1455* (2006.01)
  *A61B 5/0205* (2006.01)
  *A61B 5/02* (2006.01)
  *A61B 5/024* (2006.01)

(52) U.S. Cl.
  CPC ............ *A61B 5/7271* (2013.01); *G06F 19/345* (2013.01); *G06F 19/3431* (2013.01); *A61B 5/7435* (2013.01)

(56) References Cited

U.S. PATENT DOCUMENTS

| | | | |
|---|---|---|---|
| 2007/0106127 A1* | 5/2007 | Alman ........................... | 600/300 |
| 2008/0162182 A1* | 7/2008 | Cazares et al. .................... | 705/2 |
| 2008/0242955 A1 | 10/2008 | Uutela et al. | |
| 2009/0093686 A1 | 4/2009 | Hu et al. | |
| 2009/0105550 A1* | 4/2009 | Rothman et al. ............. | 600/300 |
| 2010/0056880 A1* | 3/2010 | Cho et al. ...................... | 600/301 |
| 2010/0179394 A1 | 7/2010 | Sohn et al. | |
| 2010/0298678 A1* | 11/2010 | Klomhaus ..................... | 600/344 |
| 2011/0137134 A1* | 6/2011 | Hemmerling et al. ........ | 600/301 |
| 2012/0053433 A1* | 3/2012 | Chamoun et al. ............. | 600/324 |
| 2012/0130198 A1* | 5/2012 | Beaul ........................... | 600/300 |
| 2013/0211858 A1* | 8/2013 | Ohnemus et al. ................. | 705/3 |
| 2014/0114680 A1* | 4/2014 | Mills et al. ........................ | 705/2 |

OTHER PUBLICATIONS

P.J. Napier, Nrao, Socorro, Medical and Physiological for a High Altitude MMA Site, Oct. 10, 1996, pp. 1-14, MMA Memo No. 162, J.B. West, School of Medicine, UCSD, San Diego.

D.R. Goldhill, A.F. McNarry, G. Mandersloot and A. McGinley, A physiologically-based early warning score for ward patients: the association between score and outcome, Anaesthesia, 2005, vol. 60, pp. 547-553, Blackwell Publishing Ltd., UK.

* cited by examiner

|  | OLTP System<br>Online Transaction Processing<br>(Operational System) | OLAP system<br>Online Analytical Processing<br>(DataWarehouse) |
|---|---|---|
| Source data | Operational data, OLTPs are the original source of data | Consolidation data; OLAP data comes from the various OLTP databases |
| Purpose of data | To control and run fundamental business tasks | To help with planning, problem solving and decision support |
| What the data reveals | A snapshot of ongoing business processes | Multi-dimensional views of various kinds iif business activities |
| Inserts and updates | Short and fast inserts and updates initiated by end users | Periodic long-running batch jobs refresh the data |
| Queries | Relatively standard and simple queries returning relatively few records | Often complex queries involving aggregation |
| Processing Speed | Typically very fast | Depends on the amount of the data involved; batch data refreshes and complex queries may take many hours, query speed can be improved by creating indexes |
| Space requirements | Can be relatively small if historical data is archived | Larger due to the existence of aggregation structures and history data |
| Database design | Highly normalized with many tables | Typically de-normalized with fewer tables |
| Back up and recovery | Back up religiously, operational data is critical to run the business, data loss is likely to entail significantly money loss and legal liability | Instead of regular backups, some environments may consider simply reloading the OLTP data as a recovery method |

Figure 3

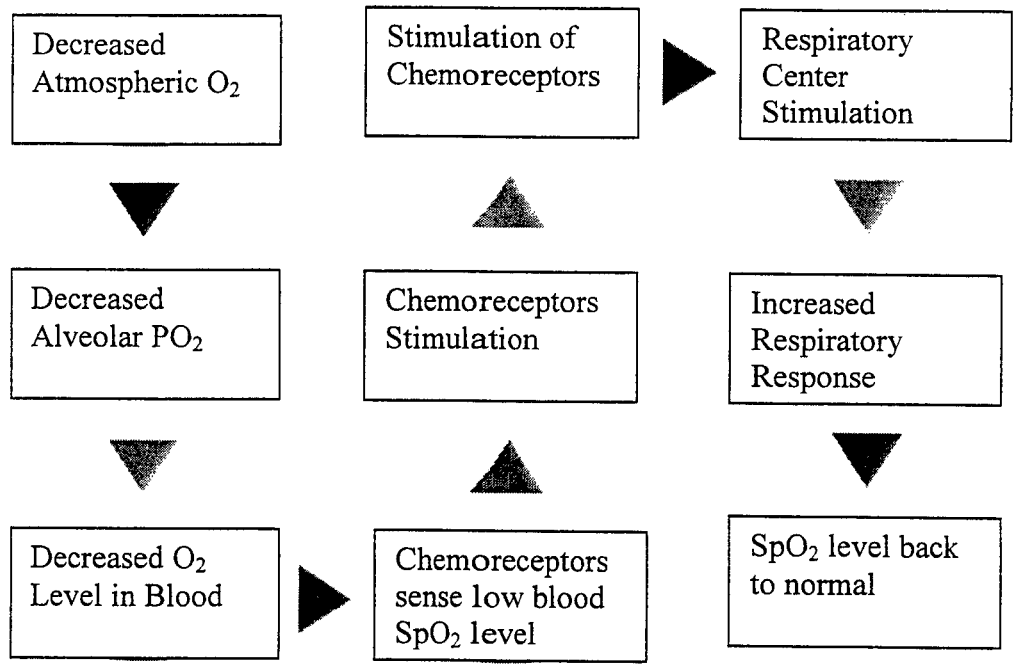
Figure 4: Respiratory response to decreased SpO2 level
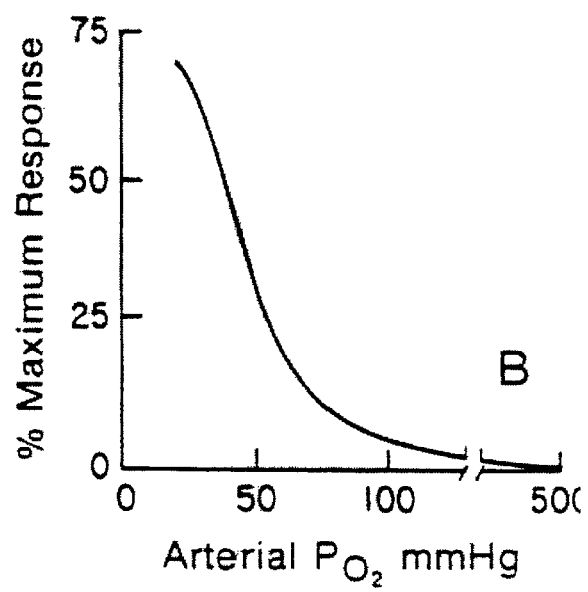
Figure 5: Relationship between SpO2 and respiratory response

| Respiratory rate (bpm) | Category / Band |
|---|---|
| less than 5 or more than 30 | Group I |
| 21 to 30 | Group II |
| 6 to 9 | Group III |
| 10 to 12 and 18 to 20 | Group IV |
| 13 to 17 | Group V |

Figure 6

| SpO2 (%) | Category / Band |
|---|---|
| 0-74 | Group I |
| 75-84 | Group II |
| 85-94 | Group III |
| 95-96 | Group IV |
| 97-98 | Group V |
| More than 98 | Group VI |

Figure 7

| Age | 18-25 | 26-35 | 36-45 | 46-55 | 56-65 | 65+ | |
|---|---|---|---|---|---|---|---|
| Athletes | 69-75 | 69-74 | 70-76 | 70-77 | 71-76 | 70-75 | Group VII |
| Excellent | 76-81 | 75-81 | 77-82 | 78-83 | 77-81 | 76-81 | Group VI |
| Good | 82-85 | 82-85 | 83-86 | 84-87 | 82-87 | 82-85 | Group V |
| Abv avg | 86-89 | 86-90 | 87-90 | 88-91 | 88-91 | 86-89 | Group IV |
| Avg | 90-93 | 91-94 | 91-95 | 92-96 | 92-95 | 90-93 | Group III |
| Blw avg | 94-101 | 95-101 | 96-102 | 97-103 | 96-101 | 94-99 | Group II |
| Poor | 102+ | 102+ | 103+ | 104+ | 102+ | 100+ | Group I |

Figure 8a: Normal heart rate values for male subject

| Age | 18-25 | 26-35 | 36-45 | 46-55 | 56-65 | 65+ | |
|---|---|---|---|---|---|---|---|
| Athletes | 74-80 | 74-79 | 74-79 | 74-80 | 74-79 | 74-79 | Group VII |
| Excellent | 81-85 | 80-84 | 80-84 | 81-85 | 80-84 | 80-84 | Group VI |
| Good | 86-89 | 85-88 | 85-89 | 86-89 | 85-88 | 85-88 | Group V |
| Abv avg | 90-93 | 89-92 | 90-93 | 90-93 | 89-93 | 89-92 | Group IV |
| Avg | 94-98 | 93-96 | 94-98 | 94-97 | 94-97 | 93-96 | Group III |
| Blw avg | 99-104 | 97-102 | 99-104 | 98-103 | 98-103 | 97-104 | Group II |
| Poor | 105+ | 103+ | 105+ | 104+ | 104+ | 104+ | Group I |

Figure 8b: Normal heart rate values for female subject

Figure 8

| Column (Score) | 0 | 1 | 2 | 3 | 4 | 5 | 6 | 7 |
|---|---|---|---|---|---|---|---|---|
| RR | Group I <5 or >30 | Group II 21-30 | Group III 6-9 | Group IV 10-12 or 18-20 | Group V 13-17 | | | |
| SpO2 | Group I 0-74 | Group II 75-84 | Group III 85-94 | Group IV 95-96 | Group V 97-98 | Group VI >98 | | |
| HR | | Group I | Group II | Group III | Group IV | Group V | Group VI | Group VII |

Figure 9

| Total scores | Health indication | Grade |
|---|---|---|
| 1-2 | Dangerous | F |
| 3-4 | Very Poor | D |
| 5-6 | Poor | C |
| 7-8 | Below Average | B- |
| 9-10 | Average | B |
| 11-12 | Good | A |
| 13-14 | Very Good | A+ |
| 15-16 | Excellent | A* |

Figure 10

| RR (Column) | SpO2 (Column) | HR (Group) | Defined Group | Interpretations |
|---|---|---|---|---|
| I | I | I | F | d |
| : | : | : | : | : |
| I | I | III | Imp | Imp |
| : | : | : | : | : |
| I | I | IV | Imp | Imp |
| : | : | : | : | : |
| I | II | VI | C | d' |
| : | : | : | : | : |
| I | III | V | C | d' |
| : | : | : | : | : |
| I | V | II | B | a |
| : | : | : | : | : |
| I | VI | VII | B- | a |
| : | : | : | : | : |
| II | II | I | D | γ |
| II | II | II | D | γ |
| II | II | III | C | γ |
| : | : | : | : | : |
| II | IV | I | G | N/C |
| : | : | : | : | : |
| III | III | II | C | f |
| III | III | III | B- | ff |
| : | : | : | : | : |
| III | III | VII | B- | Wl |
| : | : | : | : | : |
| III | IV | VII | A | β |
| III | V | I | B- | β |
| III | V | II | B- | β |
| : | : | : | : | : |
| IV | IV | III | B- | φ' |
| IV | IV | III | B | φ |
| : | : | : | : | : |
| V | V | IV | A | φ |
| : | : | : | : | : |
| V | VI | II | B | φ' |
| V | VI | III | A | φ |
| V | VI | IV | A+ | φ |
| V | VI | V | A+ | φ |
| V | VI | VI | A* | φ |
| V | VI | VII | A* | φ |

Figure 11

|     | Example Interpretation |
| --- | --- |
| Imp | Impossible combination, error returned. No interpretation is required.. |
| WI | No definitive interpretation may be made. The parameters measured are not indicative of a particular condition or state. |
| N/C | A normal compensatory process is in place. e.g. increased RR is in place to maintain good SpO2 levels. |
| a | SpO2 & HR are in the normal range. However, an abnormal Respiratory rate has been detected. |
| a' | SpO2 level is still in the normal range. However, an abnormal Respiratory rate has been detected and HR is on the low side. |
| d | SpO2 is on the low range and HR is increased to compensate for the condition. |
| d' | SpO2 is on the low range despite increased HR to compensate for the condition. |
| f | User may be in a dangerous condition with all parameters detected to be on the low side. HR and RR are unable to compensate to improve low SpO2 level. |
| γ | SpO2 is on the low side. Both HR and RR are detected to be increasing to compensate for the condition. |
| β | All parameters indicates that the user is in a calm condition. |
| Φ | Good health condition! |
| φ' | Normal health condition. There can be more exercises to improve HR. |

Figure 12

| Respiratory rate (bpm) | Category / Band |
|---|---|
| ≤5 or ≥25 | Group I |
| 21 to 24 | Group II |
| 15 to 20 | Group III |
| 10 to 14 | Group IV |
| 6 to 9 | Group V |

Figure 36

| SpO2 (%) | Category / Band |
|---|---|
| ≤90 | Group I |
| 91-94 | Group II |
| 95-96 | Group III |
| 97-98 | Group IV |
| 99-100 | Group V |

Figure 37

| Age | 18-25 | 26-35 | 36-45 | 46-55 | 56-65 | 65+ | |
|---|---|---|---|---|---|---|---|
| | ≤59 | ≤59 | ≤60 | ≤60 | ≤61 | ≤61 | Group VIIb |
| | 60-68 | 60-68 | 61-69 | 61-69 | 62-70 | 61-69 | Group VIIa |
| Athletes | 69-75 | 69-74 | 70-76 | 70-77 | 71-76 | 70-75 | Group VII |
| Excellent | 76-81 | 75-81 | 77-82 | 78-83 | 77-81 | 76-81 | Group VI |
| Good | 82-85 | 82-85 | 83-86 | 84-87 | 82-87 | 82-85 | Group V |
| Abv avg | 86-89 | 86-90 | 87-90 | 88-91 | 88-91 | 86-89 | Group IV |
| Avg | 90-93 | 91-94 | 91-95 | 92-96 | 92-95 | 90-93 | Group III |
| Blw avg | 94-101 | 95-101 | 96-102 | 97-103 | 96-101 | 94-99 | Group II |
| Poor | 102+ | 102+ | 103+ | 104+ | 102+ | 100+ | Group I |

Figure 38a: Normal heart rate values for male subject

| Age | 18-25 | 26-35 | 36-45 | 46-55 | 56-65 | 65+ | |
|---|---|---|---|---|---|---|---|
| | ≤64 | ≤64 | ≤64 | ≤64 | ≤64 | ≤64 | Group VIIb |
| | 65-73 | 65-73 | 65-73 | 65-73 | 65-73 | 65-73 | Group VIIa |
| Athletes | 74-80 | 74-79 | 74-79 | 74-80 | 74-79 | 74-79 | Group VII |
| Excellent | 81-85 | 80-84 | 80-84 | 81-85 | 80-84 | 80-84 | Group VI |
| Good | 86-89 | 85-88 | 85-89 | 86-89 | 85-88 | 85-88 | Group V |
| Abv avg | 90-93 | 89-92 | 90-93 | 90-93 | 89-93 | 89-92 | Group IV |
| Avg | 94-98 | 93-96 | 94-98 | 94-97 | 94-97 | 93-96 | Group III |
| Blw avg | 99-104 | 97-102 | 99-104 | 98-103 | 98-103 | 97-104 | Group II |
| Poor | 105+ | 103+ | 105+ | 104+ | 104+ | 104+ | Group I |

Figure 38b: Normal heart rate values for female subject

Figure 38

|  | 1 | 2 | 3 | 4 | 5 | 6 |
|---|---|---|---|---|---|---|
| RR | ≤5 & ≥25 | 21 to 24 | 15 to 20 | 10 to 14 | 6 to 9 | |
| SpO2 | ≤90 | 91 to 94 | 95 to 96 | 97 to 98 | 99 to 100 | |
| HR | Groups 1 & 2 | Group 3 | Group 4 | Group 5 | Group 6 | Group 7 — Sub-group 7a / Sub-group 7b |

Figure 39

|  | 1 | 2 |  | 3 | 4 | 5 | 6 |
|---|---|---|---|---|---|---|---|
| RR | ≤5 & ≥25 | 21 to 24 | 6 to 9 | 15 to 20 | 10 to 14 | | |
| SpO2 | ≤90 | 91 to 94 | | 95 to 96 | 97 to 98 | 99 to 100 | |
| HR | Groups 1 & 2 | Group 3 | | Group 4 | Group 5 | Group 6 | Group 7 — Sub-group 7a / Sub-group 7b |

Figure 40

| RR | SpO2 | HR | Interpretation | Score | Band |
|---|---|---|---|---|---|
| ≤5, ≥25 | 95-96 | 1&2 | a' | 44 | 7 |
|  |  |  |  |  |  |
|  |  |  |  |  |  |
| 6-9 | 99-100 | 5 | φ | 92 | 2 |
|  |  |  |  |  |  |
| 15-20 | 95-96 | 1&2 | φ' | 58 | 6 |
| 21-24 | 91-94 | 3 | γ | 56 | 6 |
|  |  |  |  |  |  |

— 3900

Figure 41 – 3-axis table (exemplary extracts only)

| Score ranges | Band | Title |
|---|---|---|
| 96 to 100 | 1 | Extremely healthy |
| 90 to 95 | 2 | Very healthy |
| 80 to 89 | 3 | Healthy |
| 70 to 79 | 4 | Average health |
| 60 to 69 | 5 | Room for improvement |
| 50 to 59 | 6 | Need to improve |
| 40 to 49 | 7 | Very unhealthy |
| 0 to 39 | 8 | Critically unhealthy |

Figure 42

| | |
|---|---|
| Imp | Due to the unusual combination of your levels of SpO2, RR and HR, we are unable to provide you with an appropriate interpretation. You may want to retake your measurements. |
| N/C | Your HR is faster due to an increase in your RR. Slowing down your RR should help in returning your HR to normal. |
| N/C' | Your HR is faster due to a decrease in your SpO2. |
| a | Your RR seems to be controlled voluntarily. Please try to breathe normally. |
| a' | Due to voluntary control of your RR, your HR is higher to compensate for the low SpO2. Please resume normal breathing to avoid any dangerous effects. |
| a" | Due to voluntary control of your RR, your SpO2 is lower than usual. |
| d | Both your HR and RR are faster to compensate for your low SpO2. |
| d' | Your body cannot cope with your low SpO2. If you are at a location of high altitude, you may want to descend to lower altitudes. Deep breathing may also help. |
| γ | Both your HR and RR are slightly faster to compensate for your low SpO2. |
| φ | Normal health condition. May also be due to your calmness or if you are in sleeping conditions. |
| φ' | Normal health condition, but with lack of exercise. HR can be improved with regular exercise. |
| z | The voluntary lowering of your RR lowers your HR, and will subsequently cause the lowering of your SpO2 as well. WARNING: this can be extremely dangerous. Please resume normal breathing immediately. |

Figure 43

|  | RR | HR | SpO2 | Band |
|---|---|---|---|---|
| Impossible | 10-20 | 4, 5, 6, 7 | < 95 | Imp |
|  | ≤ 5 , ≥ 25 | 3, 4 | ≤ 90 | Imp |
|  | 21 - 24 | 7 | ≤ 90 | Imp |
|  |  | 6, 7 | 91 – 100 | Imp |
| Atypical | ≤ 5 , ≥ 25 | 5, 6, 7 | 95 – 100 | 5 |
|  | 21 - 24 | 6 | ≤ 90 | 6 |
|  |  | 3 | 95 – 98 | 6 |
|  | 15 - 20 | 3 | 91 – 96 | 6 |
|  |  |  | 97 – 100 | 5 |
|  | 10 – 14 | 1&2, 3 | 95 – 100 | 5 |
|  | 6 – 9 | 6, 7 | ≤ 90 | 8 |
|  |  |  | 91 – 94 | 7 |
|  |  | 6 | 95 – 96 | 2 |
|  |  | 3 | 95 – 96 | 6 |
|  |  |  | 99 – 100 | 5 |

Figure 44

METHOD AND APPARATUS FOR DERIVING A HEALTH INDEX FOR DETERMINING CARDIOVASCULAR HEALTH

BACKGROUND AND FIELD OF THE INVENTION

This invention relates to a method and apparatus for deriving a health index which is used to determine cardiovascular health of a subject, particularly but not exclusively of a human subject.

There have been proposed methods which provide a scoring or charting system to determine an indication of a patient's health. Such a scoring or charting system might be able to provide general health information of a patient or user but is unable to provide specific health information. Further, such a scoring system requires the information to be interpreted by a health care practitioner and without which the information would not be understood by the patient. In addition, the scoring systems require at least one manual parameter input, such as a visual interpretation of the patient's level of consciousness, before an indication of the patient's health is obtained. In such systems, the input parameter is subject to the health practitioner's interpretation and can therefore be unreliable or inconsistent.

It is an object of the present invention to provide a method and apparatus for deriving a health index for determining cardiovascular health which alleviates at least one of the disadvantages of the prior art and/or to provide the public with a useful choice.

SUMMARY OF THE INVENTION

In accordance with a first aspect of the present invention, there is provided a computer implemented method of deriving a health index for determining cardiovascular health of a subject; the method comprising
  (i) obtaining values of at least two parameters from a PPG signal of the subject, the at least two parameters including SpO2 and at least one other parameter;
  (ii) assigning a score based on the values of the at least two parameters from a reference scoring system; and
  (iii) deriving the health index based on the assigned score.

An advantage of the described embodiment is that the at least two parameters of the PPG signal of the subject are functionally put together since the health index is derived based on the assigned score of the collective combination of parameters and this provides a much simpler and more efficient way of determining an overall health condition of a subject, in particular the cardiovascular health.

It should be appreciated that the described embodiment may be used for human and/or animal subjects.

Preferably, the PPG signal is measured or obtained non-invasively.

Preferably, the at least one other parameter is selected from the group consisting of heart rate and respiratory rate. The assigned score of the collective combination of parameters may be used to derive the health index to represent the cardiovascular health of the subject. Specifically, the assigned scores may be added to derive the health index. In the alternative, combinations of the parameter values are used to derive the assigned score.

The reference scoring system may be derived from a matrix of the at least two parameters, wherein values of the at least two parameters are mapped to respective cells associated with respective preliminary scores. The preliminary scores may be associated with respective preliminary bands; and the method further includes adjusting the preliminary scores and/or preliminary bands to derive the reference scoring system.

The reference scoring system may include a plurality of groupings for each parameter, and each grouping includes a range of readings for the respective parameter. Each combination of groupings is associated with a corresponding score for assigning to, and dependence on, the obtained values of the individual parameters. Deriving the health index at (iii) may include deriving a preliminary health index from the groupings for each parameter based on the obtained values and verifying if combination of the groupings is medically possible. The method may further comprise adding up the assigned scores to derive the preliminary health index.

If the combination of the groupings is medically not possible, the method may display an error message as the health index and suggest user to take a new set of measurements for the parameters. On the other hand, if the combination of the groupings is medically possible, the method may further include verifying if the preliminary health index requires adjustment.

If adjustment is needed, the method may include adjusting the preliminary health index to a revised health index and using the revised health index as the health index.

Preferably, verifying if the preliminary health index requires adjustment may include comparing the combination of groupings with a reference list of parameter criteria or parameter combination.

Advantageously, the at least one other parameter is categorized based on the subject's age group and gender. The health index may be associated with clinical interpretation of the cardiovascular health of the person, and the method further includes displaying the clinical interpretation as part of the health index.

Preferably, (i) further includes: illuminating a portion of living tissue of the subject and detecting transmitted or reflected light as a signal using an illumination and detection assembly; detecting an amount of pressure applied by the portion of living tissue of the subject to the illumination and detection assembly; correlating the quality of the detected signal with the amount of applied pressure; and providing feedback related to the correlation to the subject.

The method may further comprise providing an indication of whether the amount of pressure being applied to the illumination and detection assembly should be adjusted. The method may further comprise displaying a range of optimal applied pressures along with actual applies pressure being applied by the subject.

Preferably, the method further comprises displaying a range of optimal applied pressures which corresponds to a state of zero transmural pressure. Advantageously, the PPG signal is obtained when the applied pressure is at its optimal.

In accordance with a second aspect of the invention, there is provided a method of deriving a health index for determining cardiovascular health of a subject; the method comprising
  (i) obtaining values of at least two parameters from a PPG signal of the subject, the at least two parameters including SpO2 and at least one other parameter;
  (ii) assigning a score based on the values of the at least two parameters based from a reference scoring system; and
  (iii) deriving the health index based on the assigned scores.

In accordance with a third aspect of the invention, there is provided apparatus for deriving a health index for determining cardiovascular health of a subject, the apparatus comprising a processor configured to obtain values of at least two parameters from a PPG signal of the subject, the at least two parameters including SpO2 and at least one other parameter; to assign a score based on the values of the at least two parameters from a reference scoring system; and to derive the health index based on the assigned score.

The apparatus may be in the form of a mobile phone.

In accordance with a fourth aspect of the invention, there is provided a reference scoring system for determining cardiovascular health of a subject, the system comprising
(i) a first array of categories with each category representing a range of typical heart rates of subjects;
(ii) a second array of categories with each category representing a range of typical respiratory rates of subjects;
(iii) a third array of categories with each category representing a range of typical SpO2 levels of subjects;
wherein each category of a said array is associated with a score; and wherein the combinations of each of the categories of heart rate, respiratory rate and SpO2 when combined together is associated with a health index for determining the cardiovascular health of the subject.

In accordance with a fifth aspect of the invention, there is provided a reference scoring system for determining cardiovascular health of a subject, the system comprising
(i) a first array of categories with each category representing a range of typical heart rates of subjects;
(ii) a second array of categories with each category representing a range of typical respiratory rates of subjects;
(iii) a third array of categories with each category representing a range of typical SpO2 levels of subjects;
wherein combinations of the categories of the first, second and third arrays are associated with respective scores; and wherein each score provides a health index for determining the cardiovascular health of the subject.

Indeed, either of the above reference scoring systems may be used as part of a method for deriving a health index and this form a sixth aspect of the invention in which there is provided, a computer implemented method of deriving a health index for determining cardiovascular health of a subject, the method comprising
(i) obtaining values of SpO2, heart rate and respiratory rate from one or more PPG signals of the subject,
(ii) assigning a scored based on the obtained values from a reference scoring system of either the fourth or fifth aspect; and
(iii) deriving the health index based on the assigned score.

According to a seventh aspect, there is provided a method of deriving a reference scoring system for determining cardiovascular health, the method including
listing all possible permutations of at least two parameters for a PPG in a list, each permutation corresponding to a band classification and a score;
checking the list against a list of impossible and atypical combinations;
identifying which of the possible permutations in the list falls within the list of impossible and atypical combinations and marking the identified possible permutations;
manipulating the band classification of the atypical combinations;
manipulating the scores corresponding to the manipulated band classifications based on predefined scores and band classification relationships; and
deriving the reference scoring system based on the list of possible permutations and the manipulated scores and bands.

It should be apparent that features applicable for one aspect may also be applicable for the other aspects.

BRIEF DESCRIPTION OF THE DRAWINGS

An example of the invention will now be described with reference to the accompanying drawings, in which:

FIG. 3 is a table which list features of OLTP Tables and OLAP Tables used in a database of FIGS. 1 and 2;

FIG. 4 is a flow diagram illustrating respiratory response of a user to decreased SpO2 level;

FIG. 5 is graph illustrating relationship between SpO2 levels and respiratory response of a person;

FIG. 6 is a table to illustrate categorization or grouping of readings of reference respiratory rates of subjects;

FIG. 7 is a table to illustrate categorization or groupings of readings of reference SpO2 levels of subjects;

FIG. 8 comprises FIGS. 8a and 8b which are tables illustrating categorization or groupings of readings of heart rates for male and female respectively;

FIG. 9 illustrates a reference scoring system in chart form which comprises the categorizations of FIGS. 6 to 8 to show the correlation of each of the parameters;

FIG. 10 is a table to obtain a health indication based on scores obtained from the reference scoring system of FIG. 9;

FIG. 11 is a table which illustrates a list of permutations of the different combinations of the groups of the parameters of FIG. 8 and their respective medical interpretations;

FIG. 12 is a legend describing the respective medical interpretations of FIG. 11;

FIG. 36 is a table to illustrate categorization or grouping of readings of reference respiratory rates of subjects as part of another reference scoring system according to a second embodiment;

FIG. 37 is a table to illustrate categorization or groupings of readings of reference SpO2 levels of subjects as part of the reference scoring system of the second embodiment;

FIG. 38 comprises FIGS. 38a and 38b which are tables illustrating categorization or groupings of readings of heart rates for male and female respectively as part of the reference scoring system of the second embodiment;

FIG. 39 is a table illustrating how values of the parameters of FIGS. 36-38 are associated with each other;

FIG. 40 is a table illustrating how values of the parameters of FIGS. 36-38 are associated with each other as a variation of the table of FIG. 39;

FIG. 41 is a "three-axis" table as part of the reference scoring system listing exemplary permutations of the combinations of the parameters of FIGS. 36-38 and including Score and Band variables;

FIG. 42 is a health indication table providing preliminary health indications for corresponding score values and bands of the Score and Band variables of FIG. 41;

FIG. 43 is a table of a legend describing the preliminary health indications of FIG. 42;

FIG. 44 is a table showing permutations, including those not shown in FIG. 41, of the parameters which results in impossible or atypical combinations;

DETAILED DESCRIPTION OF PREFERRED EMBODIMENT

Figure 1:
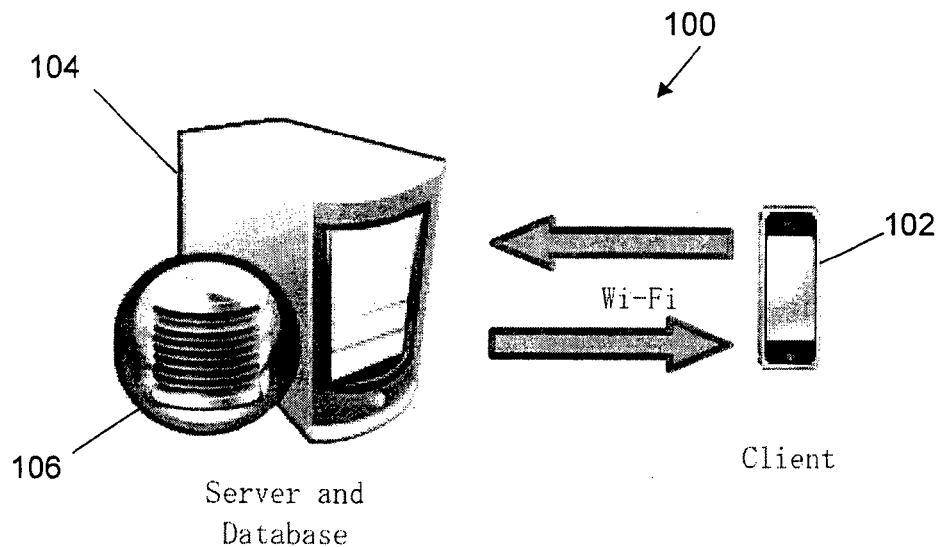
FIG. 1 illustrates a system/apparatus for deriving a health index/indication for determining cardiovascular health of a person according to a preferred embodiment which is based on respiratory rate, blood oxygen saturation SpO2 level and heart rate of the person.
Figure 2:
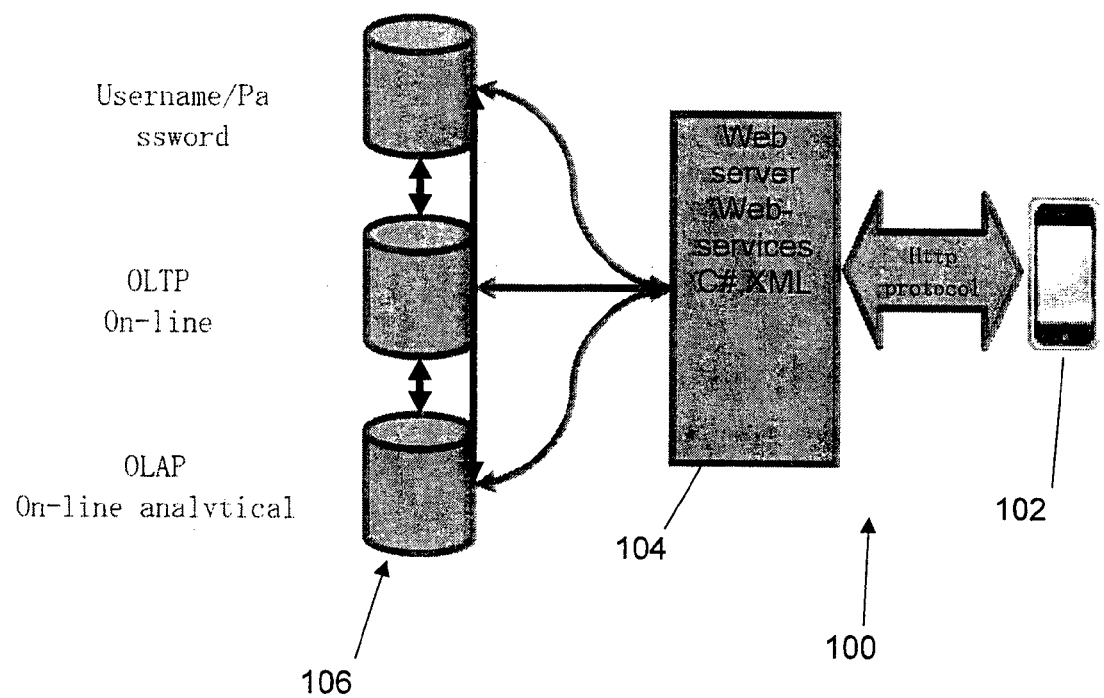
FIG. 2 illustrates a block diagram representation of the system of FIG. 1.

FIG. 1 shows a system 100 for determining cardiovascular health of a user according to a preferred embodiment. The system 100 includes an electronic device such as a mobile telephone 102 and a web server 104 communicatively coupled to the mobile telephone 102 via HTTP protocol or other wireless transmission protocol. The web server 104 is communicatively coupled to a primary database 106. FIG. 2 is a block diagram representation of FIG. 1 and shows a configuration of the primary database 106.

It should be appreciated that although the mobile telephone 102 is connected wirelessly to the server 104 in this embodiment, wired connection is envisaged.

Further, other electronic devices are envisaged, such as laptops, PDA's, tablets, PCs etc, and not necessarily a mobile telephone 102.

In this embodiment, the mobile telephone (client) 102 has a processor and is attached to a measurement unit to obtain a physiological signal from the user and an example of such a signal is photoplethysmography (PPG) signal. An example of such a mobile telephone 102 is disclosed in U.S. patent application Ser. No. 13/010,705 the content of which is incorporated herein by reference. It is also envisaged that the measurement unit may be integrally formed with the mobile telephone.

When the PPG signal of the user is obtained, parameters from the PPG signal are derived from the PPG signal and the parameters are transmitted to the web server 104 using the HTTP protocol. The mobile telephone 102 as the client retrieves information using for example, a 'GET' method and transfers information (i.e. including the parameters) to the web server 104 using for example, a 'POST' method.

In this embodiment, the web server 104 is a Windows Server™ 2008 and the primary database 106 is implemented using MySQL to provide advantages in cost and simplicity as it is able to support XML web services without any additional interface. As a result, the web server 104 is configured to communicate with the database 106 using web services such as C# and XML, for example, when requested by the user. An advantage of using such web services to communicate with the database 106 is to increase security and for data archiving. The web services are configured to access the database, store/retrieve data, perform the required analytical processing such as obtaining a social ranking (in comparison with the rest of the population) and can send the results back to the client i.e. mobile telephone 102.

As shown in FIG. 2, the database 106 is configured with OLTP (Online Transactional Processing) Tables for instantaneous or rapid data processing to respond immediately to user requests and OLAP (Online Analytical Processing) Tables which stores historical data and enables large amounts of data to be accessed in an intuitive and rapid manner. In this way, the system 100 is simple and efficient when responding to user requests. FIG. 3 is a table which list the features of the OLTP Tables and OLAP Tables.

The database 106 may be configured to serve multiple users, typically in thousands, who may be asynchronously communicating with the database (via the web server 104) to store and retrieve data at any time of the day. The database 106 is therefore able to instantaneously allow a user to obtain his/her data or parameters e.g. Heart rate, Respiratory rate, SPO2 readings and his/her current standing in the social network. Further, the database 106 may also provide the user with historical information such that he/she can identify his health trend.

It should be appreciated that a variety of parameters may be obtained from the user to provide information regarding the user's health and this may be the user's heart rate, respiratory rate, blood oxygen saturation level (SpO2), blood pressure and body temperature etc. These parameters may be individually monitored and readings obtained to provide information on the user's health. However, it is unpredictable to functionally combine such known parameters and provide a combined health index since there is no means available to decipher how the combined parameters relate to each other in order to provide meaningful health information to the user.

As a result, in this embodiment, it is proposed to provide a reference scoring system or chart which bridges the gap between selected parameters of the user and meaningful health information for the user to rely on by collectively analyzing values of the parameters in order to provide the meaningful health information.

In this embodiment, the reference scoring system is based on three parameters of the user: SpO2, respiratory rate and heart rate, and realization of how these parameters are related which is discussed below:

SpO2 and Respiratory Rate

Blood oxygen saturation level (SpO2) depends on partial pressure of oxygen in the atmosphere. If the SpO2 level is decreased, the body's physiologic system responds in order to maintain the normal level of SpO2 level in the blood, ensuring sufficient oxygen supply to the vital organs and peripheral tissues.

One physiologic response to low SpO2 level is a change in the respiratory rate of the person. When there is low oxygen level inside the blood, the peripheral chemoreceptors (carotid and aortic bodies) are activated which increases the rate of respiration. Hypoxic drive via the chemoreceptors increases the rate of respiration. A flow chart showing the respiratory response to decreased SpO2 level is as shown in FIG. 4.

As it can be appreciated from FIG. 4, the peripheral chemoreceptors situated in the carotid and aortic bodies sense the decrease in blood oxygen level. When the blood oxygen saturation is decreased due to decrease in atmospheric oxygen, the chemoreceptors are activated and they discharge impulses to stimulate the respiratory centers in the person's brain, causing increased ventilation. As a result, SpO2 returns to normal.

Therefore, there is an inverse relationship between SpO2 levels and respiratory rate when SpO2 level is below the normal values and this is illustrated in a graph of FIG. 5.

As shown in FIG. 5, when there is decreased alveolar PO2, arterial PO2 falls and in response, the respiratory minute volume is stimulated to increase. The stimulation is slight when the PO2 of the inspired air is more than 60 mmHg. At lower PO2 values, the stimulated respiration rate is appreciably increased for the same decrease in PO2 levels.

SpO2 and Heart Rate

The cardiovascular system and the respiratory system are connected to each other via blood gases such as blood oxygen level, carbon dioxide level, etc. Low SpO2 causes hypoxic stimulation of the peripheral chemoreceptors in carotid and aortic bodies which in turn causes an increase in heart rate, when the ventilation is allowed to increase.

Therefore, there is also an inverse relationship between SpO2 levels and heart rate.

Three Way Relationship of Three Parameters

It is realized that the heart rate and respiratory rate are not directly related to each other. However, given that both heart and respiratory rates are respectively related to SpO2, SpO2 may act as a link between heart rate and respiratory rate, in order to create a balanced physiological environment for body organs and system.

Reference Scoring System Based on Three Parameters for PPG Reading

To derive the scoring system, each of the parameters SpO2, heart rate and respiratory rate is categorized using readings obtained through experiments or clinical studies.

An example categorization process for the respiratory rate, heart rate and SpO2 is as follows:

i) Respiratory Rate

For respiratory rate, in this embodiment, the readings of respiratory rates are divided into a number of different categories or bands to derive a RR table which is shown in FIG. 6. As it can be appreciated, there are five groups—Group I to V, where Group V defines the best respiratory rate and Group I defines the poorest respiratory rate. Groups I and II are in the zone of abnormal RR, where it is not healthy, while groups III, IV, and V are normal ranges of RR.

ii) SpO2

Categorization of SpO2 readings is based on partial pressure of oxygen (PaO2) and the corresponding levels of SpO2, and level of sensory and mental impairment. Clinically, PaO2 of 80-100 mmHg is the normal level which corresponds to SpO2 of 95-100%. Therefore, this range of SpO2 is defined as the acceptable range. Further, to extract good and above average health conditions, the 95-100% range is broken into smaller categories, where SpO2 of 97-98% and SPO2 of 99-100% are grouped into respective categories. At lower than 95% SpO2 levels, sensory and mental impairments may occur. At SpO2 levels of between 91-94%, minimal sensory impairment may occur. At 90% or lower SpO2 levels, mental impairment begins to occur and the subject could be in critical condition and require immediate assistance. Based on these realizations, clinical data or readings of SpO2 are divided into different categories or bands to derive a SpO2 table as shown in FIG. 7, which has five groups comprising Groups I to V, where group V defines the best SpO2 measurement and group I defines the poorest SpO2 measurement. Similar to RR, groups I and II of SpO2 are abnormal and may be harmful to a person's health, while groups III, IV, and V are considered as normal and healthy SpO2.

iii) Heart Rate

Heart rate varies with age and gender. As such, categorizations are provided for various age groups and gender accordingly. Generally, normal heart rate is 20 bpm higher than the resting heart rate. Normal heart rate charts for men and women is divided into seven groups as shown in FIGS. 8a and 8b which comprises Groups I to VII. For HR, Groups I and II, as well as group III, are considered to be not so healthy, while groups IV, V, VI, and VII are the normal and healthy ranges.

As it can be appreciated from FIGS. 8a and 8b, the values are normalized between the men and women so that they share the same grouping (for example, Group IV for ages between 18-25 for men corresponds to a heart rate of 86-89 (which is regarded as Above Average), whereas for women, this corresponds to a heart rate of 90-93 to be Above Average. In this way, the reference scoring system below is applicable for both men and women.

After the data or values of each of the parameters, respiratory rate, SpO2 and heart rate are categories into the different groupings as above, each grouping or category is assigned a score.

It is appreciated that each of the parameters, e.g. respiratory rate, SpO2 and heart rate have different importance in the determination of the cardiovascular health of a person and as such, an associated score for each group of parameter is selected.

However, for ease of use, the groupings of the parameters, respiratory rate, SpO2 and heart rate are arranged in an array with associated grades and scores and this is shown in FIG. 9, with "RR" being respiratory rate and HR being heart rate. The table of FIG. 9 shows an array of four rows by nine columns with the topmost row representing scores 0 to 7 with each score being associated with at least one group of the three parameters respiratory rate (RR), SpO2 and heart rate (HR).

As an example, a 30 year old male subject with a RR of 18, SpO2 of 96% and HR of 70 (see FIG. 8a which corresponds to Group VII) is given scores of 3 for RR, 3 for SpO2 and 7 for HR based on the reference scoring system. A final score is the combination or addition of the scores of the three parameters. Based on the same example above, the subject would have a total final score of 13.

From FIG. 9, it may be observed that the RR scores range from 0-4, SpO2 scores range from 0-5, while HR scores range from 1-7. HR has a wider score range as it is possible to determine a broader range of health from HR alone. In contrast, SpO2 has a narrower range as it is not possible to determine excellent health from very good health based on SpO2. For example, it cannot be concluded that an individual with SpO2 of 100% is necessarily healthier than an individual with SpO2 of 99%. Similarly, it is not possible to conclude that RR of 15 is better than RR of 13 or 17.

As it can be appreciated from the reference scoring system as shown in FIG. 9, the total score ranges between 1 and 16. From the final score obtained, a preliminary health indication is determined based on a health indication table of FIG. 10. For example, a total score of 1-2 yields a grade F with a health indication as "dangerous" whereas, a total score of 13-14 yields a grade of A+ and health indication of "Very Good". In other words, based on the health indication of "dangerous", the user may be advised to seek immediate medical attention, whereas "Very Good" means that the user has very good cardiovascular health.

The health index, e.g. the health indication together with the score, may then be shown on an output device such as the mobile telephone 102 of the user. An advantage is that users are thus no longer required to monitor and compare individual parameters, but need only monitor a unified health index instead.

In instances where the score of the health index for a particular user is dangerously low e.g. in the dangerous range, a trigger may be activated for example by sounding an alarm on the mobile telephone 102. Alternatively, or in addition, a local hospital or family member may be informed of the individual's condition and would react accordingly via a text or email message. The text or email message may be sent e.g. via the mobile phone 102 or the web server 104. In the example embodiment, the user may be a part of a social network, wherein the user has a social network account, and other users within the social network may be informed accordingly via the social network service provider.

The health indication with corresponding "Grades" of FIG. 10 is obtained in line with several rules, some of which are shown below:

1) If all three parameters are of the same score, an associated health indication result is returned. For example, if all three parameters have a score of 1 (II, II, I, in the order of RR, SpO2 and HR as shown in FIG. 9), the total score of 3 returns a health indication of Very Poor. If all three parameters have score of 2 (III, III, II), the total score of 6 would return a health indication of Poor. If all three parameters have a score of 3 (IV, IV, III), the total score of 9 returns a health indication of Average. If all three parameters have a score of 4 (V, V, IV), the total score of 12 would return a health indication of Good.

2) If two parameters are of the same score and the remaining parameter is of an adjacent score from FIG. 9, the final indication is determined as the grade which the two parameters fall under. For example, supposing RR and SpO2 has a score of "1" each, and HR has a score of "2" (II, II, II), the total score of 4 will return an overall D grade as shown in FIG. 10. (This is subject to rule #4 below)

3) If two parameters fall within the same score column and the remaining parameter has a score which is two scores away from the score column of the two parameters, the health indication is determined from the intermediate grade. For example, supposing RR and SpO2 each has a score of "1", while HR has a score of "3" (i.e. groups II, II and III from FIG. 9), and from FIG. 10, the final indication is determined as "Poor", or the C grade, since the total score is "5".

4) For combinations involving scores with "2" and "3", an additional grade (B−) or health indication (below average) is created. This grade lies between the C (poor) and B (average) grades as shown in FIG. 10. If two parameters have a score of "3", and one parameter has a score of "2", then the total score of "8" would be associated with the B− grade of FIG. 10 and the "below average" health interpretation would result (e.g. IV, IV, II). Also, if two parameters are associated with the score "2", and one parameter has a score of "3", likewise the B− grade is given to the total score of "7" and the "below average" health interpretation would result as shown in FIG. 10 (e.g. III, III, III).

5) If all the parameters are under their respective highest possible score, an indication of "Excellent" is obtained. In the example embodiment, this occurs for example, when RR has a score of 4, SpO2 has a score of 5, and HR has a score of 7. In the example embodiment, an "excellent" health indication is also determined when RR is given a score of 4, SpO2 is given a score of 5, and HR is given a score of 6 (V, VI, VII or V, VI, VI).

6) If one or two parameters achieve a score of "0" with the remaining one or two parameters under the adjacent score of "1", an overall F grade of FIG. 10 would always be determined because of the dangerous health situation (e.g. I, I, I).

7) To provide a more accurate health indication, an intermediate range between A and A* range for scores of 13-14 is introduced and which is associated with the Grade A+. For example, this is achieved when the parameters fall within groups V, VI, IV respectively for RR, SpO2 and HR which provides total score of 13, which corresponds to Grade A+ in FIG. 10.

It will be appreciated that the rules governing the table are not exhaustive and may be determined otherwise. Special combinations of grades/scores may require adjustments in order to provide medically accurate health indications.

Further, it should be appreciated that the rules discussed above provide a framework which validates the grading system. In other words, the "grades" are not arbitrarily derived, but are in congruence with the rules defined above.

An advantage of the present system 100 is that the health indication which is understandable by the user is presented as an indication of the user's cardiovascular health and yet the system 100 is flexible enough to provide more details which enable medical practitioners to perform follow-up actions based on the total score and/or health indication. However, it has been found that simply having the health indication from the scores may not be an accurate representation of the user's cardiovascular health since there may be permutations which do not make medical sense or there may be a need to revise the health indications to more appropriately define the health condition of the user or patient. Thus, it is preferred to check the validity of the combinations of the parameters.

This is achieved by working out the possible combinations or permutations in the table of FIG. 9 and combining them with the different health indications/grades of FIG. 10 and a result is illustrated in FIG. 11 which is a table showing the some of the permutations of RR, SpO2, HR, Define group and their corresponding Interpretations.

FIG. 11 is a non-exhaustive table illustrating some of the possible combinations. FIG. 12 is a legend which explains what each of the characters under "Interpretations" represents.

For example, with reference to numeral 1102 of FIG. 11, for the RR, SpO2 and HR combination of I, I and I, a corresponding interpretation "d" and Grade (or group) "F" is obtained. Based on the FIG. 12, an interpretation "d" indicates that for such a combination, the SpO2 is on the low range and HR is increased to compensate for the condition. Numeral 1104 of FIG. 11 shows combination I, II and IV having an interpretation of "Imp", which from FIG. 12 indicates that the combination is an impossible one, and that no defined group and interpretation may be provided.

Numeral 1106 of FIG. 11 shows an example combination with an associated interpretation "a", and a Grade "B−". From FIG. 12, it should be appreciated that the interpretation "a" indicates that the SpO2 is in the normal range but an abnormal respiratory rate (RR) is detected with heart rate (HR) on the low side. An interpretation of "γ" suggests that SpO2 is on the low side and both HR and the RR are detected to be increasing to compensate for the condition. An example of this is illustrated at numeral 1108, where the combination of RR-II, SpO2-II and HR-I or II is associated with a Grade "ID" and an interpretation of "γ".

Numeral 1110 of FIG. 11, shows an example combination of parameters associated with the interpretation "N/C" which represents that a normal compensatory process is in place (see FIG. 12). The combination represented by numeral 1110 is also given a grade "C".

An interpretation of "f" indicates that the user may be in a dangerous condition since all the parameters are detected to be on the low side and an example is shown at 1112 for groups III, III and II. The combination is also given a grade "C".

An interpretation of "β" indicates that the parameter combinations show that the user is in a calm condition and an example is shown at 1114 corresponding to III, IV and VII respectively for RR, SpO2 and HR. The combination is also given a grade "A".

An interpretation of "φ" indicates that the parameters show that the user is in a good health condition and an example is illustrated at 1116. This is for example associated with parameters RR, SpO2 and HR having values which fall within the groups V, VI and VI respectively. In another example, the symbol "φ" is also used to represent parameters having groups V, V and IV, as shown in numeral 1118. In this combination, a grade A is given.

As it can be appreciated, the grades from FIG. 10 and the permutations of the parameters are analysed to provide the medical interpretation illustrated in FIG. 11 and the above are examples of those grades which may not be adjusted or manipulated by the system. On the other hand, the following examples are grades which are adjusted accordingly.
Combinations being Auto Manipulated by the System 100

1) For interpretations of d', the upper limit of the health indication cannot exceed C. Therefore, the system subtracts the final score accordingly if the final score points exceed the upper limit of 'C' band and the maximum health band would be 'C' band. For example, take the combination RR (Group I), SpO2 (Group II) and HR (Group VI), according to FIG. 9, this yields corresponding scores of 0+1+6=7 points and referring to FIG. 10, the Grade is B—and the Health Indication is "Below Average". However, the system 100 would revise the Grade according to FIG. 11 to give a C grade with the interpretation as d' 1120. This is because since one of the parameters is in the "dangerous" category (RR is in Group I which is considered "dangerous"), the system downgrades the grade to a lower health grade automatically before presenting the revised grade C to the user.

2) For interpretations of "a", the upper limit of the health indication cannot exceed B−, Therefore, the system 100 subtracts the final score accordingly if the final score points exceed the upper limit of the 'B−' band. The maximum health band thus will be the 'B−' band (e.g. I, VI, VII=12 points, but subtracted into B− grade as shown at 1122 of FIG. 11.

3) For interpretations of f', the upper limit of the health indication cannot exceed 'B'. Therefore, the system subtracts the final score accordingly if the final score points exceed the upper limit of the 'B' band. The maximum health band thus will be the 'B' band (e.g. V, VI, II=11 points, but subtracted into the B grade at 1124 of FIG. 11). In another example, for RR=group IV, SpO2=group IV and HR=group II which gives a score of 8, this converts to a grade of "B−" in FIG. 10 and as shown in FIG. 11 at 1126, there is no adjustment made since the grade is within the upper limit of the "B" grade.

4) For interpretations of WI, the health indication must be 'B−'. Therefore, the system 100 subtracts the final score accordingly if the final score points exceed the upper limit of the 'B−' band so as to avoid in giving wrong interpretations. (e.g. III, III, VII=10 points, which is Grade B from FIG. 10, but this is downgraded or subtracted to the B− grade at 1128 of FIG. 11)

These considerations are based on the possible physiology responses of body.
Automanipulation of Algorithm by the Software As described above, it is recognized that simply counting the total scores may result in inaccurate determination of the health indication and interpretation. As such, the software algorithm should take into account these special scenarios/combinations of scores and perform the necessary score adjustments, in order for a more accurate representation. In the example embodiment, the software will first match the combinations of three parameters with FIG. 11 to determine if the combination is a "normal combination" where no manipulation is needed or the combination falls within a "special combination" which requires manipulation before the information is presented to the user. In other words, if the system 100 detects a special combination, predefined score points are subtracted from the total score such that after adjustments, the final score can accordingly provide a more accurate health indication.

In addition, if the software detects some impossible combinations, error messages will be displayed on the screen. For example, a person's respiratory rate cannot be very low e.g. 5 bpm, while the SpO2 is normal e.g. in the >95% range.

If the combination does not match with any of special combinations or impossible combinations, then the total score can be directly calculated (i.e. "normal combination") and the associated health indication will be shown accordingly.

An explanation of how the user of the mobile telephone 102 obtains his cardiovascular health information will now be described using FIG. 1 and FIG. 13, which illustrates a method 1300 illustrating various steps to provide the health index.

Figure 13:
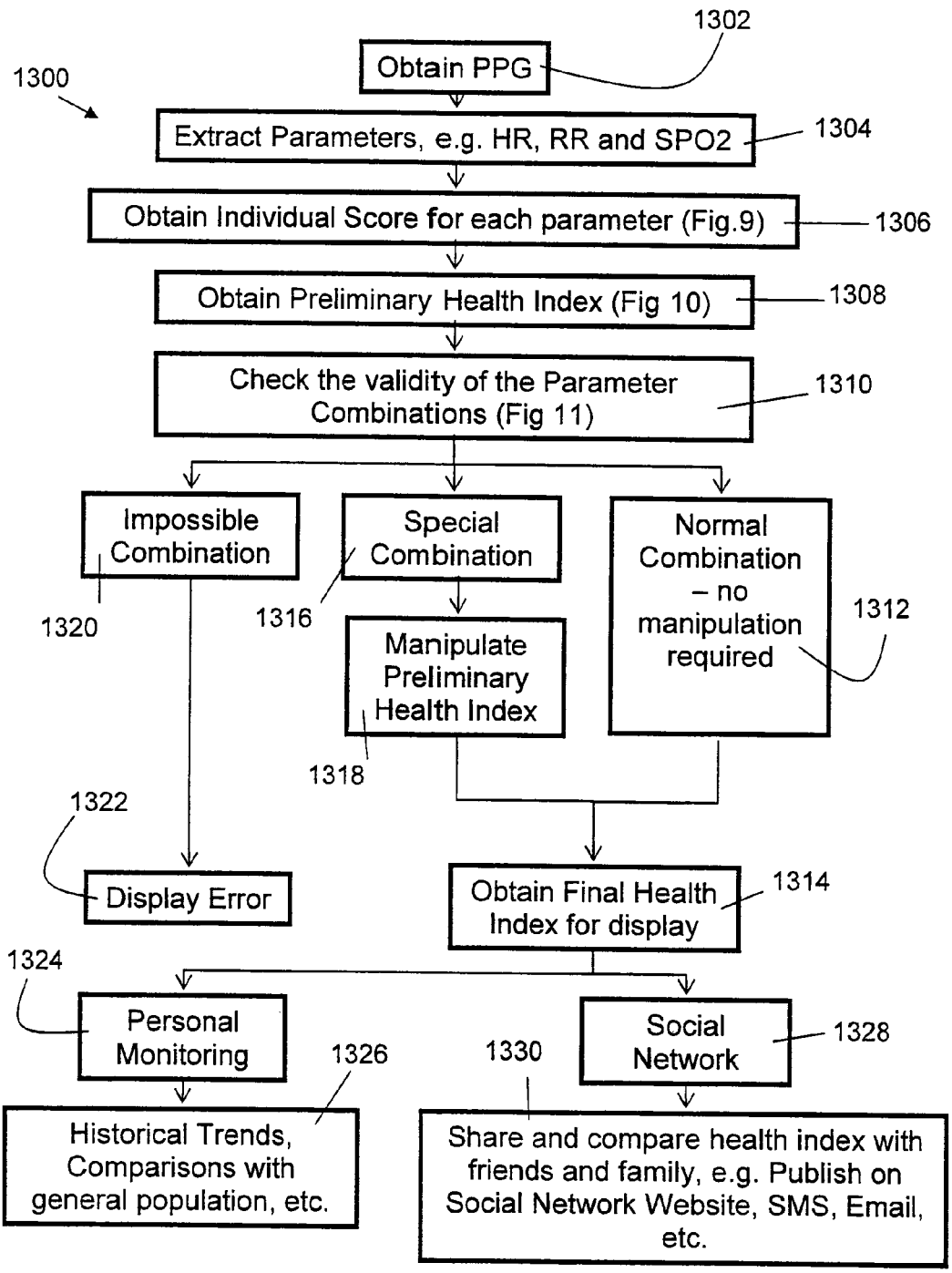
FIG. 13 is a flowchart illustrating steps of a method to provide the health indication of FIG. 1.

Referring to FIG. 1, and at step 1302 of FIG. 13, the user obtains his one or more PPG signals using known means, for example a measurement unit coupled to the mobile telephone 102. The mobile telephone 102 at step 1304 extracts the user's respiratory rate RR, SpO2 and heart rate HR from the one or more PPG signals, and at step 1306, the mobile telephone 102 look up and obtain the respective scores from the scoring system of FIG. 9 for each of the parameters.

It is also envisaged that instead of storing the scoring system of FIG. 9 at the mobile phone 102, it may be possible to store the scoring system at the database 106 (in addition to storing historical parameter data at the database 106).

Based on the respective scores associated with each parameter from FIG. 9, a preliminary health index based on FIG. 10 is derived at step 1308. Specifically, assume that the values of RR, SpO2 and HR obtained by the mobile telephone 102 fall within the following groups:

RR—Group II—score 1
SpO2—Group II—score 1
HR—Group III—score 3.

These give a total score of 5 which means that the Grade from FIG. 10 is "C" with a poor Health Indication, this being the preliminary health index.

The mobile phone 102 next checks the validity of the parameter combinations at step 1310 from FIG. 11 and in this instance, this gives a Grade of "C" which corresponds to that of FIG. 10 and the Symbol "γ" at 1130 of FIG. 11 which gives an interpretation that the SpO2 is on the low side and both HR and RR are detected to be increasing to compensate for the condition.

In other words, this falls within the "Normal Combination" i.e. step 1312 of FIG. 13, and thus, no manipulation is needed. The method 1300 thus proceeds to use the Grade "C" and the associated health indication "Poor" as the health index and provide this to the user at step 1314, for example via the display of the mobile phone 102. It is also envisaged that the health index may be in the form of the "Total scores" of FIG. 10 which is presented to the user. Also, it is possible that health index is represented by both the total scores and the health indication of FIG. 10. Further, the health index may also comprise the grade and/or the corresponding medical interpretation which is presented to the user.

On the other hand, instead of Group II, Group II and Group III for RR, SpO2 and HR respectively, another set of readings are obtained instead. For example, assuming that the readings of RR, SpO2 and HR give the following groups: Group I, Group III and Group V. These give scores of 0+2+5=7. According to FIG. 10, this should give a Grade of "B−" i.e. below average. However, based on FIG. 11 at 1132, the Grade of "B−" is not consistent with the Grade "C" given in FIG. 11 for the same combination of groups of parameters and thus, the method 1300 goes to step 1316 which falls within the "Special Combination". At step 1318, the method 1300 manipulates the preliminary health index obtained at step 1308 by downgrading this to Grade "C", consistent with that shown in FIG. 11, and displays this to the user at step 1314. In this way, the health index is adjusted accordingly to better reflect the user's health condition.

In a further alternative, it is assumed that the readings of RR, SpO2 and HR give the groupings: Group I, Group I and Group III and according to FIG. 10, the Grade is "D"—very poor—since the total score is "3". However, at step 1310 when this is checked against FIG. 11 at step 1134, it is noted that such a combination is "Impossible" and thus, the method 1300 branches to step 1320 and eventually to step 1322 to display an error message to the user.

As it can be appreciated from the above, these three parameters RR, SpO2 and HR are combined to provide a single marker or indication of the health condition of the subject/patient, specifically the cardiovascular health. As such, the health marker may provide a faster, more meaningful interpretation of the parameters, than if the parameters were interpreted individually.

Historical scores of an individual may also be stored in the web server 104, specifically in the database 106. This may allow a user to track his progress or monitor changes in his health score such as steps 1324 and 1326 which is for personal monitoring. For example, the scores (historical and present) may be displayed in the form of a chart, which plots the various changes in the score of the user.

The web server 104 may be configured to provide various features to assist the user. For example, the user may be provided with options to share his score with other users via e.g. publications on social networking websites or via direct messages as shown at steps 1328 and 1330. Alternatively, the user may elect to keep his identity secret, but can retrieve scores of other anonymous users such that he can compare his scores with other users. The individual's score may be presented as a percentile of the population's scores. In such an embodiment, all scores may be stored anonymously in the database 106.

The comparison may also be made with a subset of the general population. For example, the comparison may be made with a specific gender or other individuals from the same age group, or both. The user may also elect to add his score to the central database.

As described in the above embodiment, after each data or values of each parameter, respiratory rate, SpO2, and heart rate are categorized into their respective groupings, a score is assigned based on the combination of parameters.

It is appreciated that each of the parameters, eg respiratory rate, SpO2, and heart rate have different importance in the determination of the cardiovascular health of a person and as such, the associated or assigned score is based on the relative health significance of the manner of combination of parameters or when the parameters are considered collectively. Thus, a reference scoring system according to a second embodiment is envisaged which embody this variation and is independent from that proposed above, although elements described below may also be applicable for the one described earlier.

FIG. 36 is a table to illustrate categorization or grouping of readings of reference respiratory rates of subjects as part of the reference scoring system according to the second embodiment. Comparing FIG. 36 with FIG. 6, it should be appreciated that both figures are similar except that the values of the respiratory rates are slightly revised in FIG. 36. It should be appreciated that the values and ranges shown in FIG. 36 may also be used for FIG. 6 and vice versa.

FIG. 37 is a table to illustrate categorization or groupings of readings of reference SpO2 levels of subjects as part of the reference scoring system. Again, the content of FIG. 37 is similar to the one shown in FIG. 7, but consists one less group, and the values of the SpO2 are also revised. Again, values of such a table may also be used for the table of FIG. 7, and vice versa.

FIG. 38 comprises FIGS. 38a and 38b which are tables illustrating categorization or groupings of readings of heart rates for male and female respectively as part of the reference scoring system of the second embodiment. In addition to the fields and rows shown in FIG. 8, additional sub-groups VIIa and VIIb, for heart rate Group VII for both men and women are also added to the table. This is done in consideration of the fitter groups of people, such as athletes, where it is normal for those in this group to have heart rates in the range of 50 to 60 bpm. These sub-groups thus enable further distinction between the very healthy and the extremely healthy.

FIG. 39 is a table illustrating how values of the parameters of FIGS. 36-38 are associated with each other. For ease of understanding, the groupings of the parameters, respiratory rate, SpO2, and heart rate are arranged in an array of associated health significance, with "RR" being respiratory rate, and "HR" being heart rate.

In FIG. 39, an index of "1" is associated with RR of =5 and =25, SpO2 of =90, and HR is based on Groups 1 & 2 of FIG. 8 (It should be apparent that although different conventions are used, Groups 1, 2 etc in FIG. 39 correspond to Groups I, II etc of FIG. 38). On the other hand, an index of "5" is associated with RR of 6 to 9, SpO2 of 99 to 100, and Group 6 of FIG. 39. For example, based on FIG. 39, RR of 17 would be deemed to have equal health significance as SpO2 of 95 and HR belonging to Group 4.

FIG. 40 is a table illustrating how values of the parameters of FIGS. 36-38 are associated with each other as a variation of the table of FIG. 39. It should be appreciated that FIGS. 39 and 40 are similar where the vertical columns depict the correlated health significance of the three parameters, with a distinction being the placement of RR having values of 6 to 9. This range of RR is unique in that it may mean both healthy and not so healthy RR, depending on the other two parameters of SpO2 and HR. When both SpO2 and HR are in the normal range, i.e. SpO2 having 95% to 100% (i.e. having any of the scores 3 to 5) and HR with Group 4 and above, RR of 6 to 9 is likely to be obtainable by the very healthy. Athletes as well as those who practice breathing exercises are better able to breathe in deeply, thus maximising oxygenation from each breath. For this reason, FIG. 39 is catered for the healthier group of users, with RR 6 to 9 being placed on the better end of the scoring spectrum.

On the other hand, for the less healthy, RR of 6 to 9 may be an indication of ill health. The segregating factor here would be if either parameter of SpO2 or HR is below normal. When SpO2 and/or HR are outside of the defined normal range, RR of 6 to 9 is taken to be below normal as well, as shown in FIG. 40. This would place RR 6 to 9 in a position slightly better than RR of 21 to 24, but still not good enough to be considered in the normal ranges of RR.

From FIGS. 36 and 37, it may be observed that RR and SpO2 have five categories each, while HR has six categories (or different indexes). HR has a wider scoring range as it is possible to determine a broader range of health from HR alone. In contrast, SpO2 has a narrower scoring range as firstly, the range of normal SpO2 in a person is rather limited, and also because it is hard to determine very good health based on SpO2 alone. For example, it is hard to conclude that an individual with SpO2 of 98% is necessarily healthier than an individual at 97%. Similarly for RR, it is hard to conclude that RR of 16 is significantly better than RR of 15 or 17.

Based on these correlation factors, a three-axis table of scores is created as part of the reference scoring system of the second embodiment and FIG. 41 shows the three-axis table and showing some of the permutations. All the possible combinations and permutations were worked out and scores were assigned based on some mathematical formulae, although only some of the combinations are shown in FIG. 41.

Figure 47A:
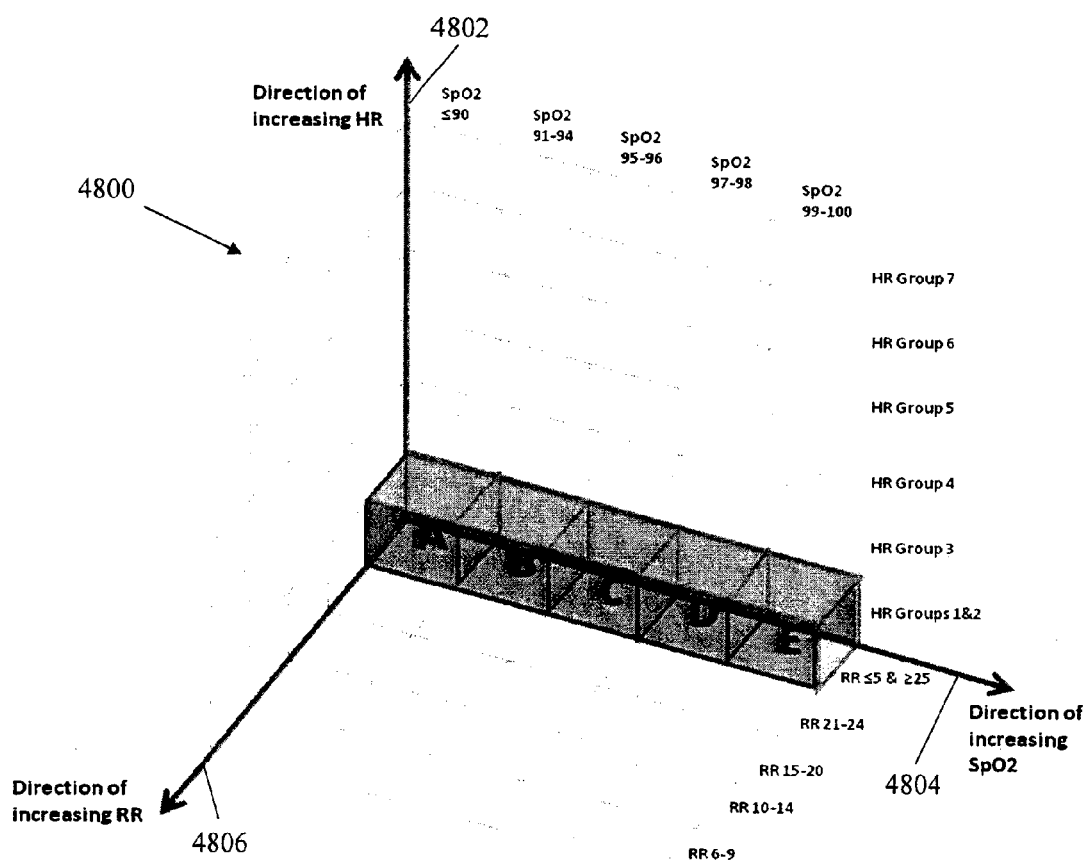
FIGS. 47a-47c illustrate 3-axis matrices to show association between parameters of FIGS. 36-38 in order to derive the 3-axis table of FIG. 41.
Figure 47B:
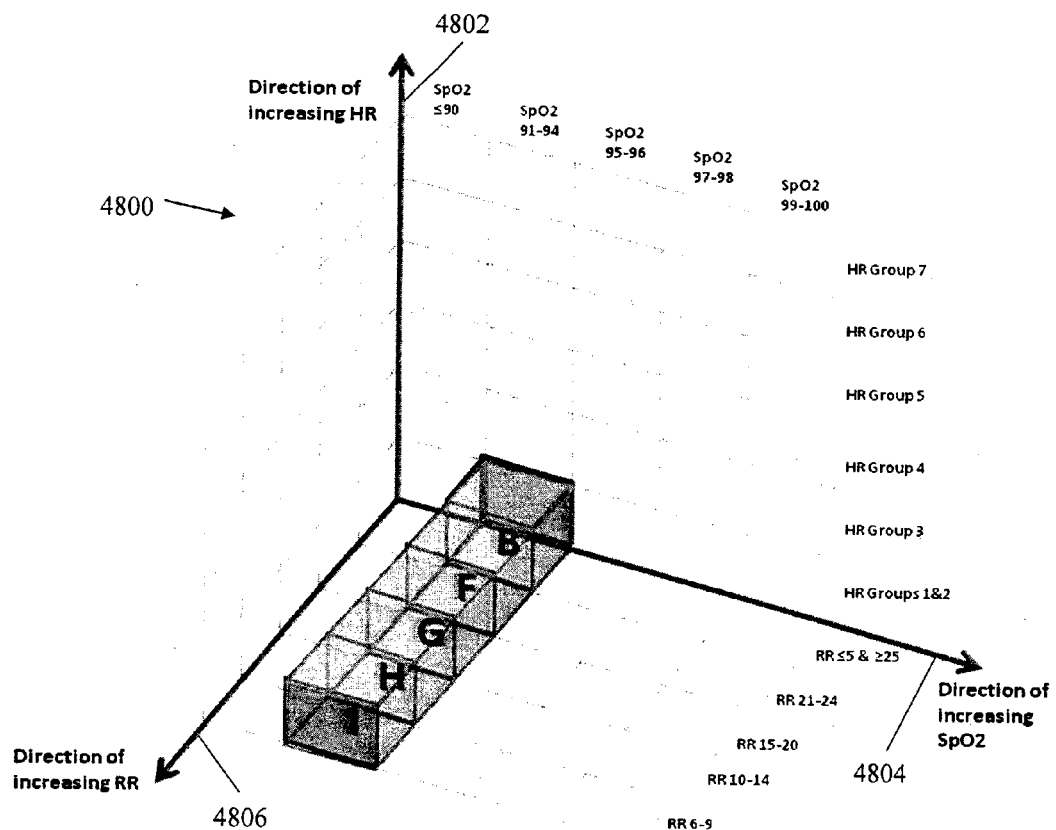
Figure 47C:
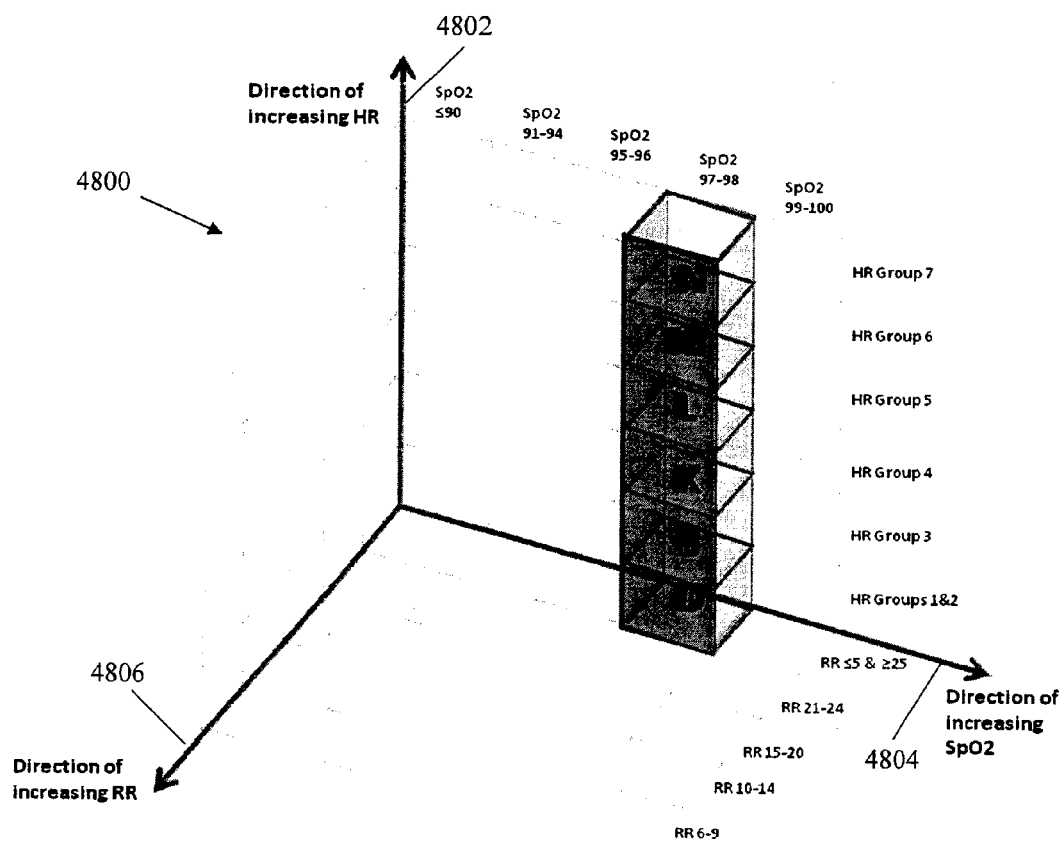

A method of creating the three-axis table of FIG. 41 is to create a three dimensional matrix 4800, where three axes 4802,4804,4806 represent the respective three parameters of RR, SpO2, and HR, and where each grid of the matrix represents a combination of parameters. FIGS. 47a, 47b, and 47c show portions of this three dimensional matrix, where cells A, B, C to N represent scores that are associated or mapped to their respective parameter ranges. For example, cell A represents the score that is associated with RR=5 & =25, SpO2=90 and HR Groups 1&2, while cell F represents the score associated with RR 21-24, SpO2 91-94 and HR Groups 1&2.

Each score is calculated based on a mathematical formula that follows a progressive change, starting from the zero axes (i.e. where all the three axes 4802,4804,4806 meet). The score of cell A of FIG. 47a may for example be −5 of the score in cell B, and score of cell B may be −4 of cell C, cell C −3 of cell D, and so on. This is repeated for every cell in each axis' direction, for example score of cell B of FIG. 47b is −5 of cell F, and cell K of FIG. 47c may be −3 of cell L, until the entire matrix is populated with scores. By this method of calculation, the score in cell A will always be the lowest score, corresponding to the combination of parameters RR=5 & =25, SpO2=90 and HR Groups 1&2 being an extremely unhealthy and critical range.

In other words, the three-axis table of FIG. 41 includes the RR, SpO2 and HR parameters and their corresponding values from FIGS. 47a-47c, and each of these range of values are associated with respective Interpretation, Score and Band.

The Interpretation column provides a medical interpretation symbol for each combination of RR, SpO2 and HR, and likewise, the Score provides a score from 0 to 100, and the Band provides a corresponding band from 1 to 8. The provision of a band and its associated score allows a useful and more meaningful indication to the user of his/her overall cardiovascular health status. For example, the score may help to provide distinctions within the same band. To elaborate, a person with a score of 75 may not be able to obtain a meaningful indication of his/her cardiovascular health and the associated band may help to clarify this. However, the person would know that his/her health would be better than someone with a score of 70, for example.

Based on the exemplary FIG. 41, a 32 year old man with respiratory rate of 9, SpO2 of 99%, and heart rate of 83, would be given a score of 92 out of 100.

As it can be appreciated from the reference scoring system discussed above, the total scores are on a scale of 0 to 100. From this score, a preliminary health indication is determined based on a health indication table as shown in FIG. 42, where each score range is associated with a band, with band 1 being the best, and band 8 the worst. For example, a score of 36 will be placed in band 8, giving a health indication of "Critically unhealthy", whereas a score of 93 will yield the health indication of "Very healthy". In other words, based on the health indication of "Critically unhealthy", the user may be advised to seek immediate medical attention, whereas "Very healthy" suggests that the user is in good cardiovascular health and should aim to maintain or further improve on his or her health.

Also depicted in FIG. 41, each combination of the parameters is associated with one of the medical interpretation symbols, based on the medical nature of each specific combination. FIG. 43 is a legend which provides an explanation or description of what each medical interpretation symbol mean, in a way similar to that of FIG. 12.

The health index, e.g. the health indication, together with the score as well as the associated interpretation, may then be shown on an output device such as the mobile telephone of the user (see FIG. 1). An advantage is that users are thus no longer required to monitor and compare individual parameters, but need only monitor a unified health index instead.

In instances where the score of the health index of a particular user is dangerously low, e.g. in the critical range, a trigger may be activated, by sounding an alarm on the mobile telephone for example. Alternatively, or in addition, a local hospital or family member may be informed of the individual's condition and would react accordingly via a text or email message. The text or email message may be sent e.g. via the mobile phone or the web server. In the example embodiment, the user may be part of a social network, wherein the user has a social network account, and other users within the social network may be informed accordingly via the social network service provider.

An advantage of the present system 100 is that the health indication which is understandable by the user is presented as an indication of the user's cardiovascular health and yet the system 100 is flexible enough to provide more details which enable medical practitioners to perform follow-up actions based on the total score and/or health indication. However, it has been found that simply having the health indication from the scores may not be an accurate representation of the user's cardiovascular health since there may be permutations which do not make medical sense or there may be a need to revise the health indications to more appropriately define the health condition of the user or patient. Thus, it is preferred to check the validity of the combinations of the parameters.

Just like FIG. 11, the table of FIG. 41 also includes permutations of the parameters which may not be medically possible or are medically possible but requires manipulation. FIG. 44 is a table showing some of these combinations (i.e. non-exhaustive) which includes those not shown in FIG. 41, and FIG. 44 illustrates combinations of the parameters, RR, HR and SpO2 which result in impossible or atypical combinations and a corresponding band. In short, there are two broad classes of combinations which may be considered as abnormal, the impossible combinations and the atypical combinations.

For the impossible combinations, these are defined by the criteria stated as medically impossible. For example, it is medically impossible to have RR of 17, with heart rate of 80 (i.e. Group 4), and SpO2 of 88%. The only chances of these combinations occurring would be if the user was voluntarily manipulating his or her bodily functions or if something highly unusual was going on in the user's cardiovascular system. In these cases, the system will prompt the user to retake their measurements by perhaps showing an appropriate message on the mobile phone 102. A band "Imp" is allocated to define the impossible combinations.

As for the atypical combinations, those that fall into this are "special" in that individually, each parameter may seem well, but in actual fact, when all three parameters are looked at together, taking into consideration their manner of correlation, the combination may be rather unhealthy, or vice versa. Thus for these combinations in the atypical zone, the bands or corresponding health indications, would have to be manipulated in order to depict a more accurate interpretation.

Examples of Combinations being Auto Manipulated by the System

Based on the criteria list shown in the table of FIG. 44, the affected combinations need to have their health bands manipulated by the system.

For the impossible combinations, all combinations that come under the impossible criteria would have their respective health band set to "Imp", and no score is assigned to the combination. As an example, the first criteria for the impossible combinations state that any combination of RR 10 to 20, SpO2 below 95% and HR in Group 4 or better is not medically possible. Referring to row 3900 of FIG. 41, it can be seen that the combination of RR 10 to 14, SpO2 91 to 94, and HR of Group 6 has been set to impossible, as stipulated by the impossible criteria.

The manipulation of atypical combinations involves more steps. Firstly, the health band will have to be modified to the appropriate band based on the criteria specified in FIG. 44. In other words, FIG. 44 specifies the band associated with each combination of the parameters and if any of the bands does not match that of FIG. 44, then the bands would be adjusted accordingly or manipulated. After the band has been set to the appropriate band, the score will then have to be manipulated as well in accordance with the corresponding band and score ranges as shown in FIG. 44. Taking row 2 of FIG. 41 as an example, since this combination of RR=5, =25, SpO2 99 to 100, and HR of Group 7 is one of the criteria in the atypical combinations criteria list, its initial health band of band 4 has now been set to band 5. Its score has also been adjusted such that it fits into the range of band 5 scores.

In another example of RR 6 to 9, SpO2=90, and HR group 7, the initial scoring would have placed this combination in band 5. However, crosschecking with the atypical criteria list in FIG. 44, this particular combination should be a band 8. Thus, FIG. 41 shows the already manipulated band of band 8, and the score that has been adjusted accordingly to 39, which falls into the band 8 scoring range.

As it can be appreciated, in this second embodiment, the manipulation of any bands and/or scores is performed earlier and the 3-axis table of FIG. 41 already includes the manipulated bands and/or scores. This is different from the earlier embodiment in which manipulation is performed each time measurements are taken and their associated scores calculated.

Using another example of using the table of FIG. 44 to change or manipulate the bands, assuming the combination of RR of 6-9, HR in group 3 and SpO2 of 99-100. FIG. 44 stipulates that this combination needs to be in band 5. Thus, if the system detects that such a combination is not in band 5, the band is manipulated so that in the table of FIG. 41, the "adjusted or manipulated" bands are shown accordingly.

Similarly, if a 43 year old woman has RR of 22, SpO2 of 97% and HR of 101 (i.e. Group II of FIG. 38b), based on the initially assigned score, she would have been assigned to band 5. Due to the atypical criteria that states any combination of RR 21-24, SpO2 97 to 98, and HR group 3 must be assigned a band 6 instead, the woman's health band and score will have to be adjusted accordingly to give a better reflection of her health status.

In FIG. 41, the shaded rows are examples of atypical combinations that were manipulated as previously mentioned, whereas non-highlighted rows are normal combinations that are not defined in the criteria list of impossible or atypical combinations. Thus no manipulation is needed for these normal combinations.

Automanipulation of Algorithm by the Software

As described above, it is recognized that simply using a generic scoring reference table may result in inaccurate determination of the health indication and interpretation. As such, the software algorithm should take into account these atypical combinations of scores and perform the necessary score adjustments, in order for a more accurate representation. In the example embodiment, the software will first identify if the combinations of the three parameters fall into the criteria range as stipulated in FIG. 44 and the bands/scores adjusted accordingly to derive the 3-axis table of FIG. 41.

Figure 46:
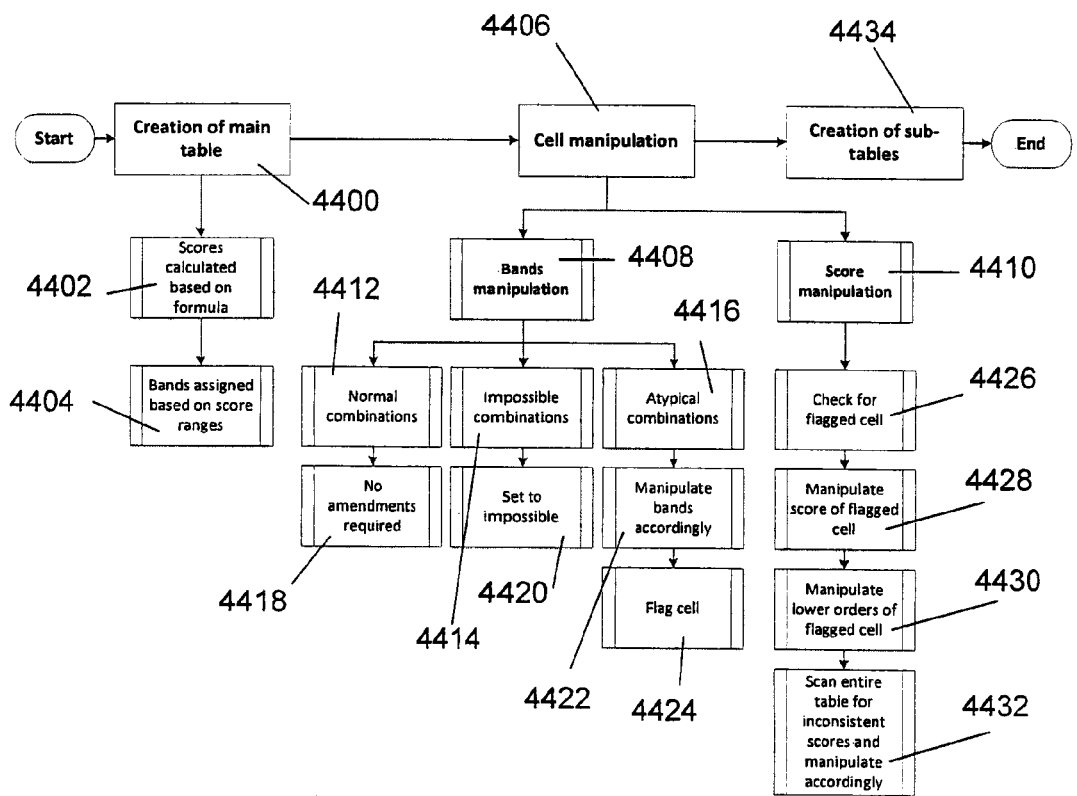
FIG. 46 is a schematic diagram of deriving a reference scoring table of FIG. 41.

The above is explained further with reference to FIG. 46 which shows a method of creation of a scoring table (for example, using a computer) such as the one including the 3-axis table of FIG. 41, manipulation of the contents of the scoring table and creation of sub-tables. First, a preliminary table comprising all possible permutations of the parameters is created at step 4400 and this includes forming combinations of the parameters based on the 3-axis matrix of FIGS. 47a-47c as explained earlier.

After the creation of the preliminary table, step 4406 is carried out to manipulate the cells of FIGS. 47a-47c, and this step is subdivided into band manipulation at step 4408 and score manipulation at step 4410. At step 4408, this creates three possible categories of permutations—Normal combinations 4412, Impossible Combinations 4414 and Atypical Combinations 4416 and this segregation is carried out by first matching each permutation of the combinations of the parameters from the preliminary table created at step 4400 against the list of criteria in FIG. 44. The combinations of the values of the parameters, RR, HR and SpO2 from the preliminary table which fall within the combinations corresponding to "Impossible" combinations would have their scores and health indication set to impossible at step 4420, while atypical combinations will have their bands manipulated accordingly at step 4422 and the combinations are then flagged at step 4424. Once all the affected combinations have had their bands adjusted accordingly, the remaining combinations are considered the normal combinations which require no amendments as shown at step 4418.

After the bands manipulation, the process moves on to the score manipulation at step 4410 for all the atypical combinations, which have been flagged. In this score manipulation process 4410, it will first check for flagged combinations at step 4426. For each flagged combination found, the score of the combination is manipulated accordingly at step 4428 based on the stipulated score ranges of FIG. 42. Other combinations that may be affected by this change in scoring will also have to be manipulated accordingly at step 4430. When all flagged combinations have been adjusted accordingly, a final scan of the entire scoring table will then be carried out to check for inconsistencies in scores and/or bands at step 4432.

The general guidelines in checking for inconsistencies are as follows:
1. The score of a better combination should have to be higher than that of a lower combination, with the tables in FIGS. 39 and 40 defining which combinations are better.
2. The score of a combination should be within the scoring range of the band assigned, based on the corresponding scores and bands as stipulated in FIG. 42.

After cell manipulation, the flow goes to step 4434 which is the creation of sub-tables. This refers to the additional combinations due to the addition of sub-groups VIIa and VIIb for heart rate of Group VII. These sub-tables are applicable where combinations involving HR Group 7 have RR and SpO2 that are within normal ranges. This then completes the procedure of creating the 3-axis table of FIG. 41 as part of the reference scoring system.

Figure 45:
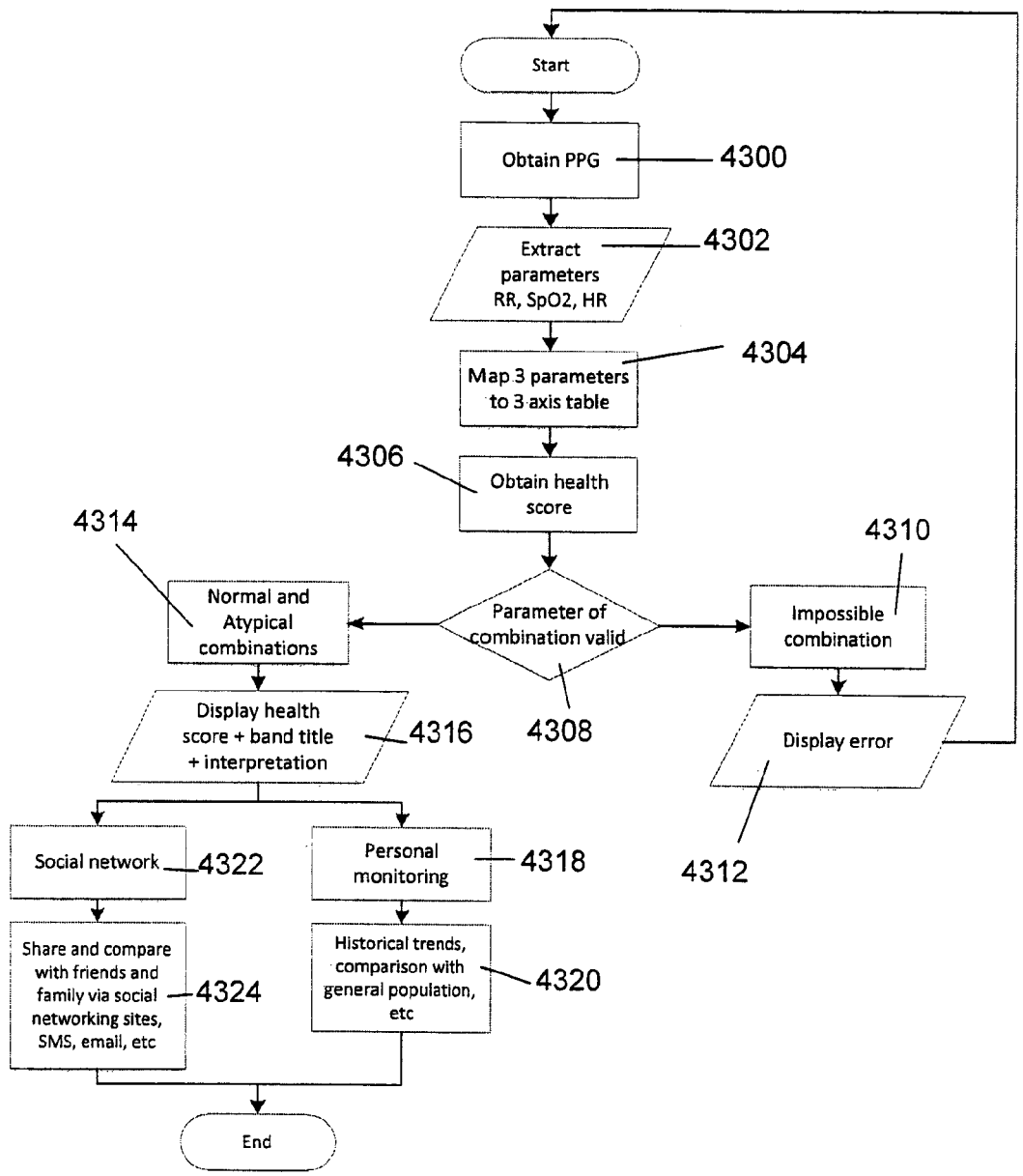
FIG. 45 is a flow chart illustrating steps of a method to provide the health indication using the table of FIG. 41.

FIG. 45 is a flow chart illustrating a method explaining how the user of the mobile telephone 102 of FIG. 1 obtains his cardiovascular health information based on the table of FIG. 41.

Similar to FIG. 13, at step 4300, the user obtains his PPG signal using known means, for example a measurement unit coupled to the mobile telephone 102. The mobile telephone 102 at step 4302 extracts the user's respiratory rate RR, SpO2 and heart rate HR from the PPG signal, and at step 4304, the mobile telephone 102 maps the values of the three parameters to the "three-axis" table of FIG. 41 in order to derive a corresponding health score at step 4306.

It is also envisaged that instead of storing the scoring system of FIG. 41 at the mobile phone 102, it may be possible to store the scoring system at the database 106 (in addition to storing historical parameter data at the database 106).

Based on groupings in the table of FIG. 41, it is checked if the combination of the parameters falls within valid or invalid combinations at step 4308. For example, if the combination falls within any of the impossible combinations defined in FIG. 44, the mobile phone 102 returns an impossible combination at step 4310 and displays an error message at step 4312 perhaps to ask the user to recapture his PPG signal and the flow goes back to Start and eventually to step 4300 again.

At step 4308, if the validation returns a possible combination, the method goes to step 4314 to obtain the corresponding scores and band classification from FIG. 41 and the clinical interpretation from FIG. 42.

Next, at step 4316, the score, band classification and the interpretation as obtained from FIGS. 42 and 43 are displayed as the health index to the user via the mobile phone 102. It is possible the health index is represented by any of these elements, for example, only the score, or a combination of the score and band classification and how detail the health index is may depend on the maturity of the user in using this system.

Like the earlier embodiment, historical scores of an individual may also be stored in the web server 104, specifically in the database 106. This may allow a user to track his progress or monitor changes in his health score and use the information for personal monitoring as in steps 4322 and 4324. For example, the scores (historical and present) may be displayed in the form of a chart, which plots the various changes in the score of the user.

The web server 104 may be configured to provide various features to assist the user. For example, the user may be provided with options to share his score with other users via e.g. publications on social networking websites or via direct messages as shown at steps 4322 and 4324. Alternatively, the user may elect to keep his identity secret, but can retrieve scores of other anonymous users such that he can compare his scores with other users. The individual's score may be presented as a percentile of the population's scores. In such an embodiment, all scores may be stored anonymously in the database 106.

The comparison may also be made with a subset of the general population. For example, the comparison may be made with a specific gender or other individuals from the same age group, or both. The user may also elect to add his score to the central database.

Figure 14:
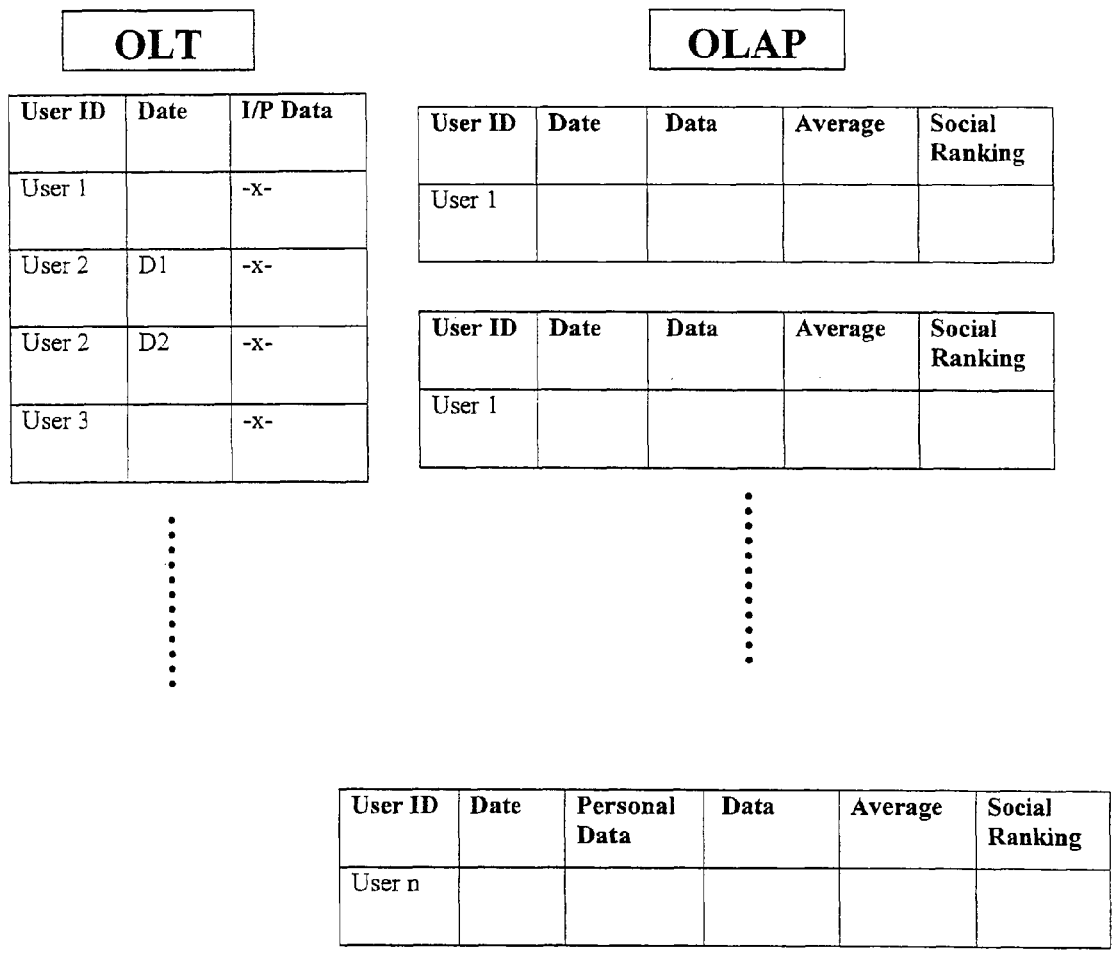
FIG. 14 shows format of the health data of users which are stored in the database of FIG. 1, which is based on the OLTP and OLAP tables.

The users' data is stored in the database may have a format shown in FIG. 14, which is based on the OLTP and OLAP tables. The OLTP Table comprises the user's current instantaneous data. The user may input multiple data points in the same day. Similarly other user's current data is also stored in the same table.

The OLAP table is configured to comprise respective tables for individual users. Their personal particulars, their daily readings, their social ranking and other particulars are stored. Each table may be different from the other and hold all the history of the user. The OLAP acts as a data warehouse for the OLTP tables and allows user information to be effectively archived for future analysis and to e.g. identify the trend of the user's health.

As explained earlier, the PPG signal may be obtained using any known means. Also, the parameters may be derived from one or more PPG signals derived from respective sources. Further, it is preferred to obtain the PPG signal based on the device as proposed in U.S. patent application Ser. No. 13/010, 705 for better accuracy, the content of which is incorporated herein by reference.

The acquisition of a physiological signal representing a change in the volume of an organ in the body through the use of optical measurement is known as a photoplethysmograph (PPG) and thus, the PPG signal is understood accordingly. Obtaining optical PPG signals typically requires application of external pressure on the body surface which is being measured. The pressure is required in order to obtain a good quality PPG signal with a high signal to noise ratio.

Figure 15:
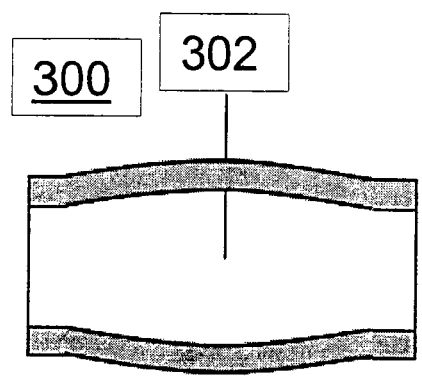
FIG. 15 is an illustration of a cross-section of a blood vessel when a low external pressure is applied.
Figure 16:
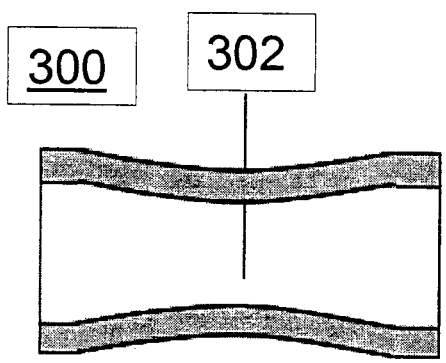
FIG. 16 is an illustration of the cross-section of the blood vessel when a high external pressure is applied.
Figure 17:
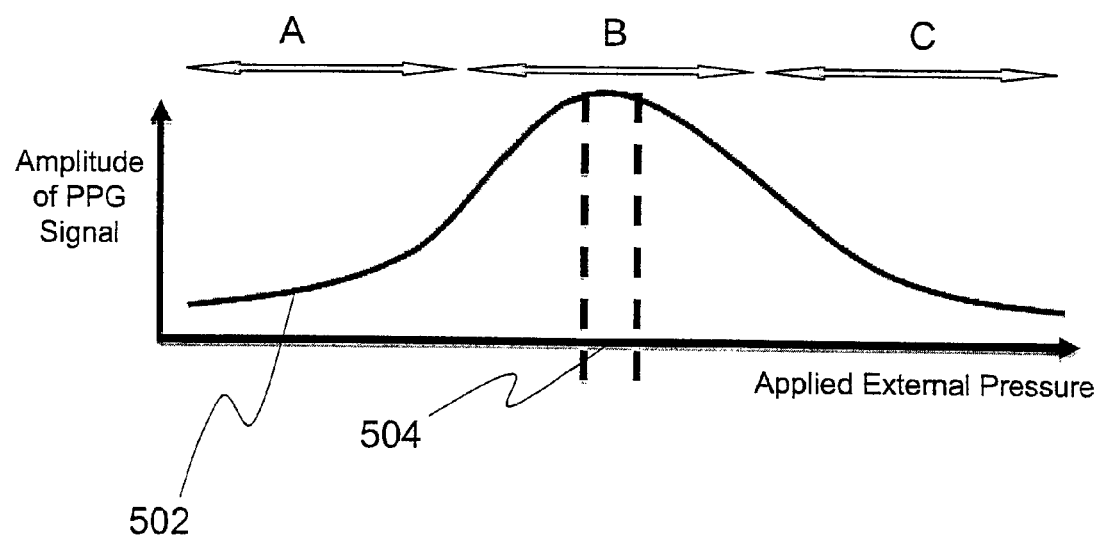
FIG. 17 is a graphical illustration of an amplitude of a PPG signal received during increasing amounts of external pressure in a state of zero transmural pressure.

However, the externally-applied pressure cannot be too large or too small, or the quality of the detected PPG signal will be low. For example, as illustrated in a cross section of a blood vessel 300 in FIG. 15, in the event of an insufficient exertion of external force as compared to internal arterial pressure at a measurement site 302, the internal pressure is too low to obtain a proper measurement, and low PPG signals are obtained. On the contrary, as illustrated in FIG. 16, the application of too much external force causes the blood vessel 300 to be occluded at the measurement site 302 where the pressure is applied, resulting in resistance of regular blood flow and generating skewed PPG signal data. If the external pressure is too small or too high, the reaction pressure at the wall of the blood vessel 300 is low, and thus a small PPG signal will be observed. FIG. 17 is a graphical illustration of the amplitude 502 of a measured PPG signal in comparison with an amount of applied external pressure. With a low applied pressure in range A, the amplitude 502 is correspondingly low. As the applied pressure is increased, in range B, the amplitude also increases. However, when the applied pressure increases beyond a certain point, the amplitude decreases again, as shown in range C.

To obtain a strong PPG signal, the external pressure should be sufficient to minimize transmural pressure such that the external pressure is equal to the internal pressure. Further illustrated in FIG. 17 is a range 504 within range B where the amplitude of the PPG signal is at its peak. Within this range 504, an externally-applied pressure is instantaneously balanced with the internal arterial pressure, thus resulting in a state of zero transmural pressure. At zero transmural pressure, the arterial walls are unloaded and the arteries will not change in size. Consequently, the blood volume within the arteries at the measured region will not change and can be accurately measured to provide a good quality PPG signal.

In this exemplary embodiment, the pressure assembly seeks to achieve and to maintain an optimal pressure for obtaining an optimum PPG signal over an extended period of time. By providing real-time, instantaneous feedback to a user being measured, the user is able to instantly adjust the amount of pressure being applied to the device in order to obtain an optimum PPG signal. However, the optimum pressure may not only be a result of a state of zero transmural pressure, but may also result from the effects of absorption and scattering paths of light as light travels in and out of a portion of tissue of a user being measured. For example, where the pressure is too low, a light source may not be able to penetrate the tissue surrounding the blood vessel which is being measured. Therefore, light may not travel in and out of the finger effectively enough for a good PPG signal to be detected. Where the pressure is too high, light may be absorbed or scattered such that the amount of light detected is insufficient to obtain a good PPG signal.

The device may also provide feedback to the user indicating whether the user is applying insufficient pressure, too much pressure or the correct amount of pressure. The feedback to the user may be visual or auditory in the form of a visual display or audible sounds, and may particularly be a display of the real-time PPG signal being captured by the device. The feedback may also be a more simplified display indicating whether the user should take action to increase or reduce the amount of pressure being applied to the device. In a variation, the feedback may be in the form of tactile feedback, wherein the device produces e.g. a small vibration when the applied pressure is at an optimum range.

Figures 18A, 18B:
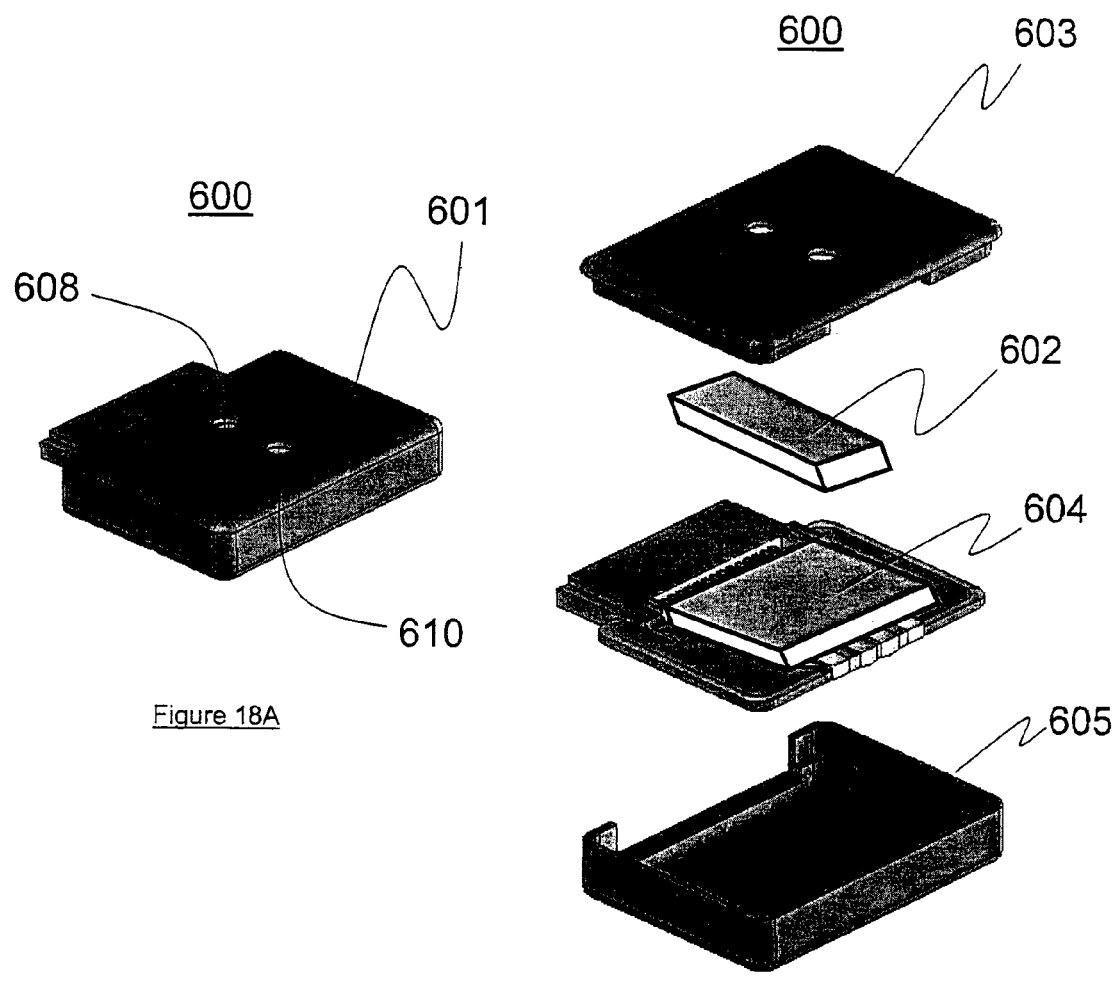
FIG. 18A is an illustration of an optical measurement device, according to an exemplary embodiment.
FIG. 18B is an exploded view of the optical measurement device of 18A, including an illumination and detection assembly and a pressure detection assembly.

FIG. 18A illustrates one exemplary embodiment of an optical measurement device 600, and FIG. 18B illustrates an exploded view of the optical measurement device 600, showing the arrangement of an illumination and detection assembly 602 and a pressure detection assembly 604. As illustrated in FIG. 18A, the illumination and detection assembly 602 and pressure detection assembly 604 may be integrated as a single, compact optical measurement device 600 surrounded by a housing 601 for portable use. In the exploded view in FIG. 18B, the housing 601 is shown divided into a top casing 603 and a base casing 605, with the illumination and detection assembly 602 and pressure detection assembly 604 enclosed therein. The integration of the pressure detection assembly 604 with the illumination and detection assembly 602 provides a simple, comfortable interaction for the user, and the use of a pressure detection assembly 604 which provides real-time feedback to the user improves the quality, or amplitude, of the received PPG signals. The optical measurement device 600 is connected with a feedback unit 606 (see FIG. 21A), which receives the PPG signals and pressure measurements from the optical measurement device 600 and provides feedback to the user regarding the amount of pressure being applied. As it can be appreciated, in this embodiment, the feedback unit 606 is in the form of the mobile telephone 102 of FIG. 1 (shown enlarged in FIGS. 21A and 21B).

The illumination and detection assembly 602 may be referred to as a PPG sensor, and includes a light source 608 and a plurality of light detectors 610 (see FIG. 29), where the light source 608 propagates light through a portion of living tissue at a measurement site of a user. The light detectors 610 then detect light which is transmitted through the portion of living tissue of the user or which is reflected from the portion of living tissue of the user.

Figure 19A:
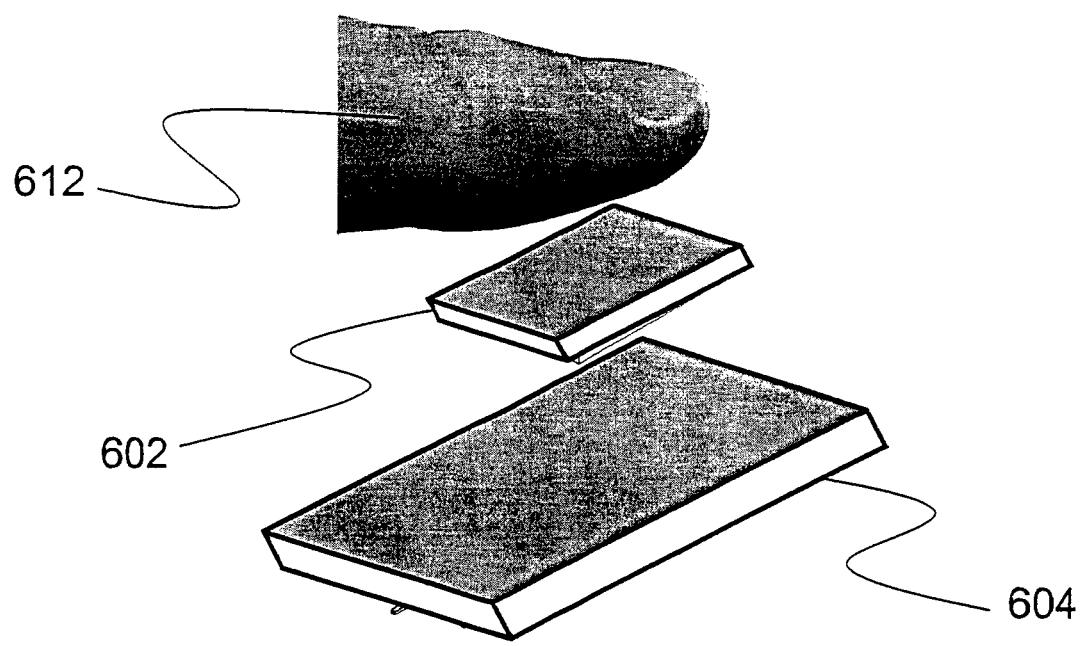
FIGS. 19A and 19B are expanded view illustrations of the illumination and detection assembly and pressure detection assembly of the optical measurement device of FIG. 18B and a method of use with a human finger.
Figure 19B:
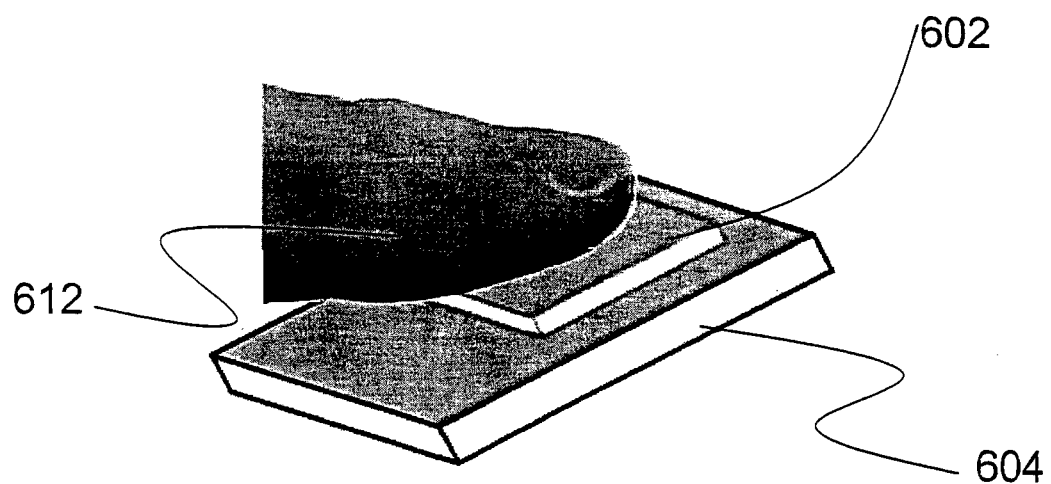

In one exemplary embodiment, the pressure detection assembly 604 is a pressure sensor that detects the amount of pressure that has been applied by a body part of the user, such as a finger. The pressure sensor may be a thin film flexible printed circuit. Nevertheless, any other force measuring device that is capable of sensing an applied contact force may be used. As illustrated in the exploded view of the optical measurement device in FIG. 19A, the pressure sensor 604 may be positioned below the PPG sensor 602, so that the force applied by a user's finger 612 is translated through the PPG sensor 602 to the pressure sensor 604. The pressure sensor 604 then gathers and tracks the external force exerted by the user's finger 612. FIG. 19B illustrates an assembled view of the pressure sensor 604 together with the PPG sensor 602 in operation, where the user's finger 606 is placed in contact with the PPG sensor 602.

Instead of a mobile telephone 102, the feedback unit 606 may be a computer including a processor, a memory and optionally a display, as is further described below with regard to FIG. 34. The feedback unit 606 receives a PPG signal and pressure measurements from the optical measurement device 600, and temporally correlates the PPG signal with the pressure measurements in order to determine an optimal amount of pressure that provides an optimal PPG signal, as shown in the comparison PPG signal graph 802 and applied pressure graph 804, illustrated in FIG. 20 and described in more detail below.

Figures 21A, 21B:
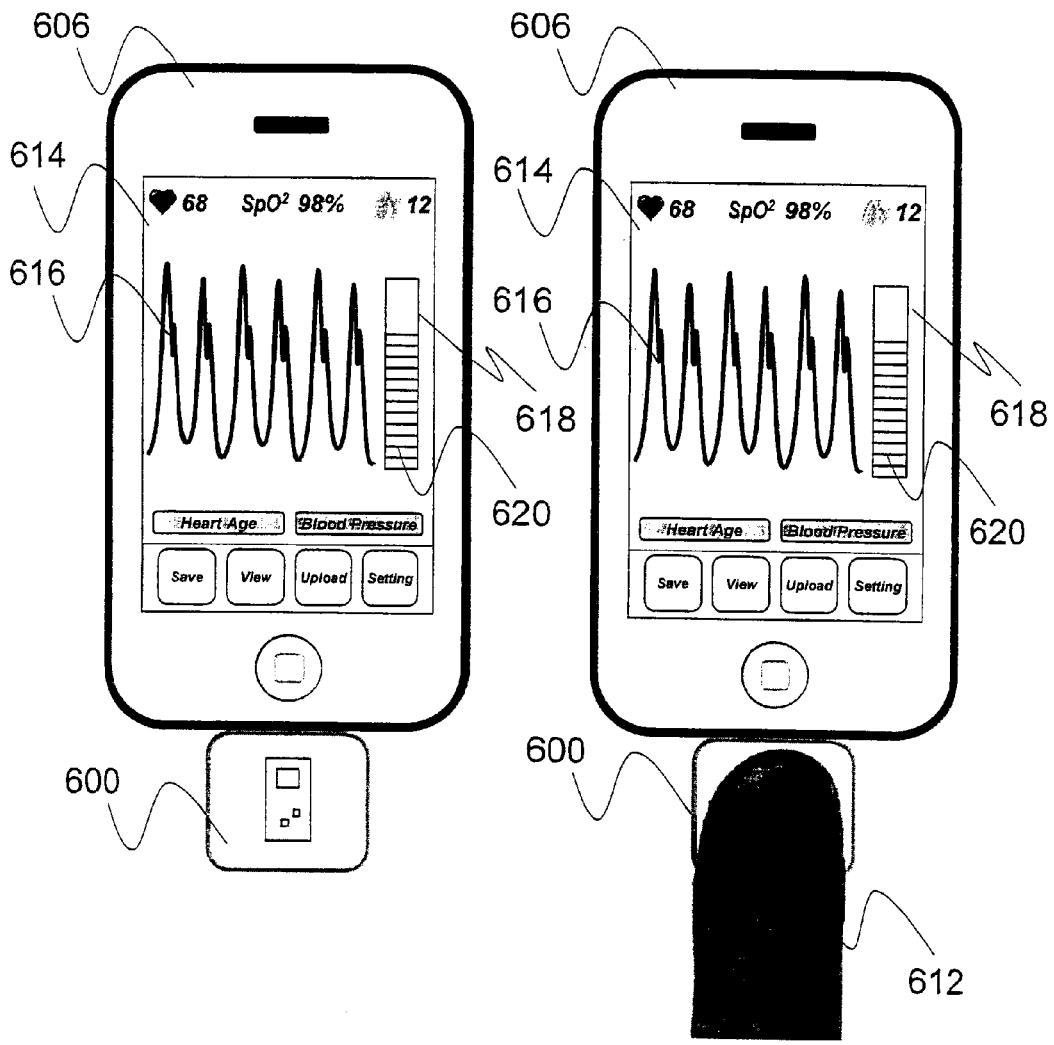
FIGS. 21A and 21B illustrate a feedback unit, such as a portable device with a display, in connection with the optical measurement device of FIG. 18A and a user's interaction therewith respectively.

The feedback unit 606 may be provided with a display 614, as illustrated in FIGS. 21A and 21B. The display 614 may provide visual feedback to the user in the form of a graphical user interface (GUI) during the process of measuring the PPG signal. The visual feedback may be a real-time display of the detected PPG signal 616 so that the user can instantly see the effect of varying the amount of pressure being applied to the optical measurement device and adjust the amount of pressure until an optimum PPG signal is displayed. The display 614 may also provide a real-time graphical indication 618 of the pressure being applied. The graphical display 618 of the applied pressure may track the PPG signal 616 on the same graphical display (see FIG. 33A, below), or perhaps be displayed in the form of a vertical pressure status bar 620 positioned on one side of the displayed PPG signal, as illustrated in FIGS. 21A and 21B. The status bar 620 will move up and down depending on the amount of force being applied by the user. In this embodiment, the user identifies an optimal PPG signal in order to determine whether the displayed real-time PPG signal 616 can be improved. However, by displaying the detected PPG signal 616 and possibly the pressure status bar 620, the feedback unit 606 is not required to compute an amount of pressure that provides an optimum PPG signal, as the user is performing this step manually by analyzing the displayed PPG signal 616 and making adjustments without guidance by the device. FIG. 21B illustrates the feedback unit 606 and the optical measurement device 600 in operation, where a user's finger 612 is positioned on the optical measurement device 600.

Figure 22:
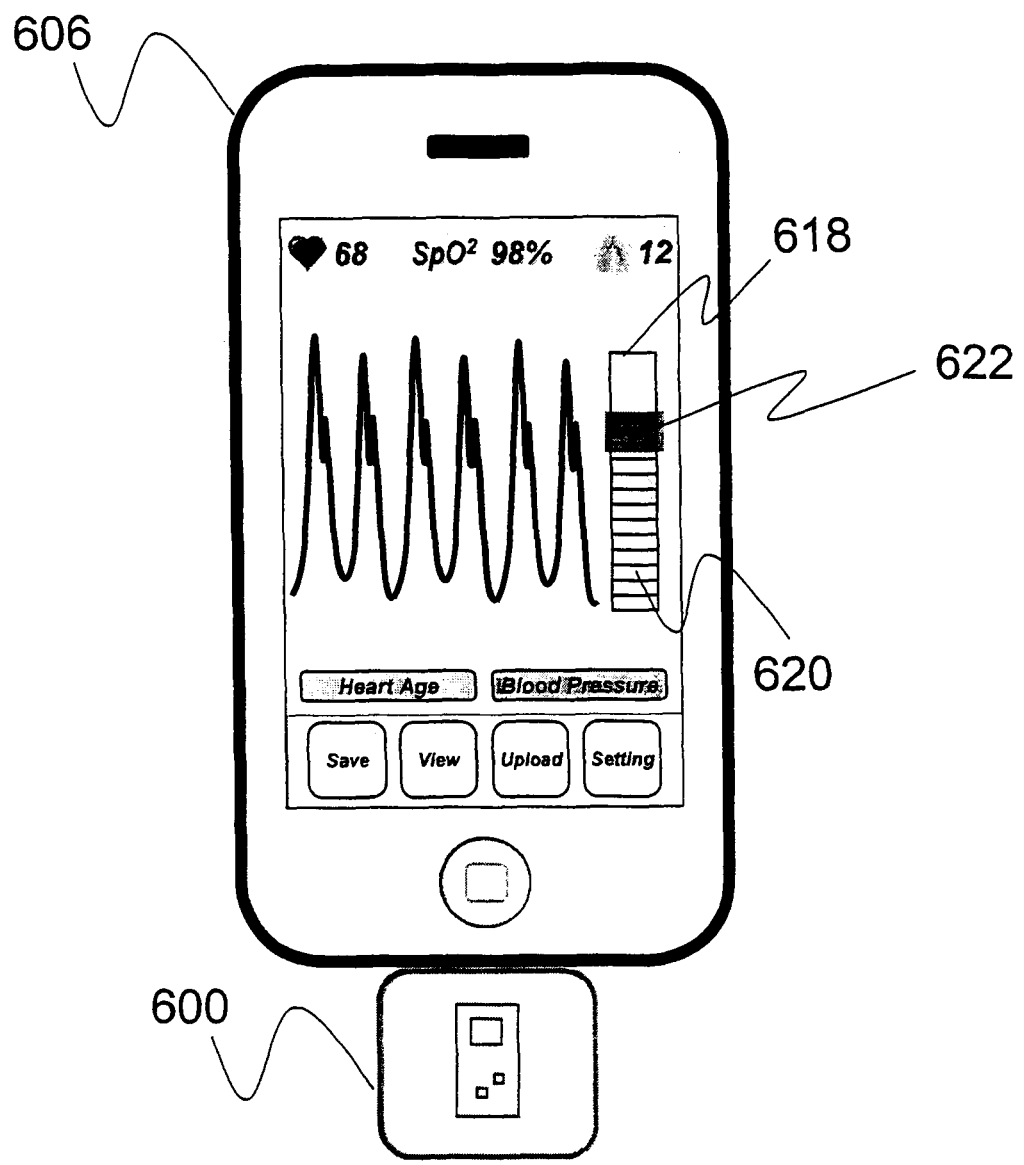
FIG. 22 illustrates a graphical user interface (GUI) on the display of the feedback unit of FIG. 21A, including a graphical representation of a PPG signal and a graphical representation of applied pressure.

In an exemplary embodiment illustrated in FIG. 22, the feedback unit 606 may generate and display a GUI with a more simplified indication of whether the user should adjust the amount of pressure to provide more, less or the same amount. There may be any number of ways to provide this type of GUI. For example, symbols or shapes—perhaps even color-coded in a traffic-light colored display—may be displayed to tell the user to adjust the amount of force being applied. Similarly, the GUI may simply display words telling the user to "Apply More Pressure, "Apply Less Pressure," or "Apply the Same Amount of Pressure." In FIG. 22, a highlighted box 622 may be placed over the pressure status bar 620 to identify an optimum range at which pressure should be applied for a particular user. In this embodiment, the feedback unit 606 analyzes and compares the measured PPG signal and corresponding applied pressures in real-time in order to determine a range of applied pressure which provides the highest amplitude of PPG signal—usually a state of zero transmural pressure. The feedback unit 606 then provides corresponding indicators to the user on the display 614 depending on whether the user is applying pressure within, above or below the determined range.

In an exemplary embodiment, the feedback unit 606 may not require a display, as it could provide audible commands to the user through a speaker or other audio output component. For example, the audio device could simply talk to the user to say "Apply More Pressure," "Apply Less Pressure," or "Apply the Same Amount of Pressure." The audio feedback could also be in the form of musical tones of different pitches or sounds—such as a ringing sound or buzzer sound—which are widely known as positive or negative sounds.

In another exemplary embodiment, the optical measurement device 600 may ask the user to calibrate the device before actual measurement of the PPG signal is carried out. This may involve asking the user to apply a variety of different pressures to the device during a fixed period of time, during which the feedback unit measures the PPG signal detected during that time period and determines a range of applied pressure which obtains an optimal PPG signal. For example, the user may be asked to exert pressure while following a profile of pressure ranges over a period of time, such as the force profile 808 in the applied pressure graph 804 in FIG. 20. As a result of the calibration, the device 600 is able to obtain a range of applied pressure for each individual user, rather than a generalized range which will not be accurate depending on the individual user being measured.

Instead of a mobile telephone, it should be appreciated that the feedback unit 606 may be any portable device, such as a smartphone, personal digital assistant (PDA), tablet, netbook or laptop, although this list is not exhaustive by any means. However, the feedback unit 606 may not need to be portable, and could similarly be a computer or server. The feedback unit 606 may be connected with the optical detection device 600 in a wired or wireless fashion, or through a proprietary connector, such a universal serial bus (USB) port or the 30 pin connection used in the Apple® iPhone® (Apple Computer, Inc., Cupertino, Calif.).

This embodiment will be described with the feedback unit and corresponding interface, processing and display for an Apple® iPhone®, although one of skill in the art will recognize that other portable devices may be used as described above.

The illumination and detection assembly 602 may be connected with the feedback unit 606, in this case a portable device such as an iPhone®, using the 30 pin connector at the base of the feedback unit 606. After establishing physical connection of the illumination and detection assembly 602 with the feedback unit 606 or any other form of processing device, a microcontroller unit (MCU) 640 (see FIG. 17) in the illumination and detection assembly 602 extracts information for authentication purposes prior to sending of data to the feedback unit 606 or any other form of processing device. This authentication process may be specific to the iPhone®, as Apple® requires that any device using the 30 pin connector purchase an authentication token from Apple®.

With the example of an iPhone®, communication is enabled via the Universal Asynchronous Receiver/Transmitter (UART) protocol from the 30 pin connector of the iPhone®. Strings of data are sent to UART every 8 milliseconds from the MCU of the illumination and detection assembly 602 to the iPhone®.

The data is comprised of 2 bytes of header and 10 bytes of payload. The payload is sub-divided into 5 parts, each comprising 2 bytes of data: DC1(IR), DC2(Red), PPG1 (IR), PPG2 (Red) and FS (Force Sensor). This data is obtained in a HEX file format and is then converted to back to voltage (V).

Figure 35:
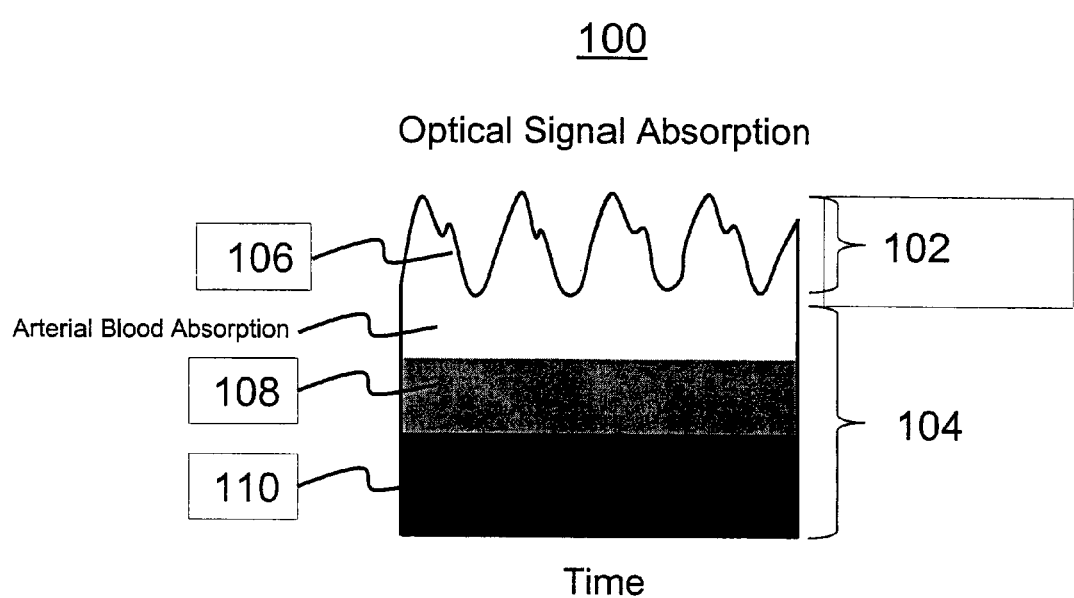
FIG. 35 is an illustration of a photoplethysmograph (PPG) and the components thereof.

Referring back to FIG. 35, DC1 and DC2 provide information for the DC component 104 of the PPG waveform, thus enabling calculation for saturation of peripheral oxygen, or SpO$_2$. PPG1 and PPG2 establish the actual PPG waveform and provide information for the AC component 102 of the PPG waveform. FS sets out to provide information of the amount of pressure applied to the illumination and detection assembly 602. An example of the data decoding format is show in Table 2, below.

Figure 32:
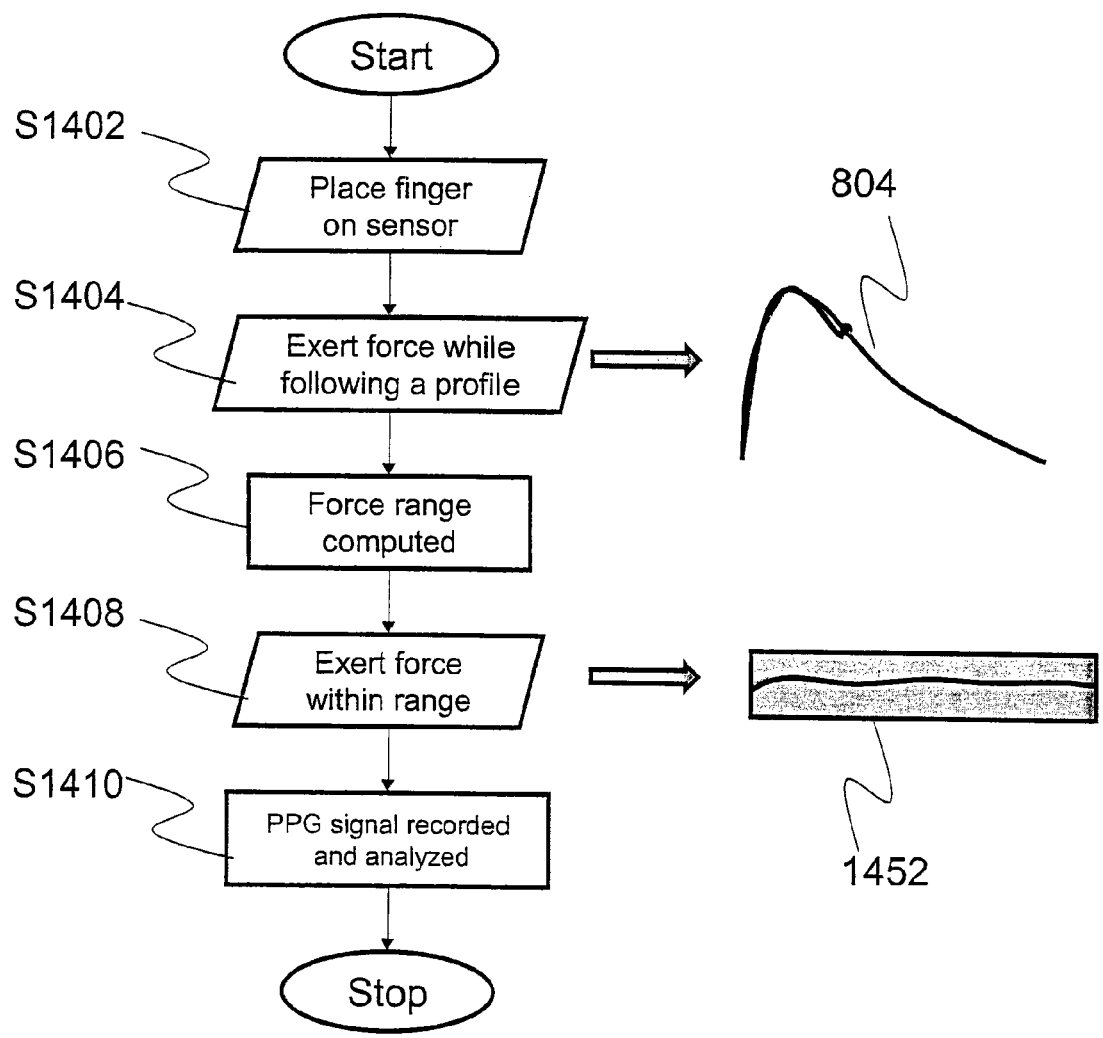
FIG. 32 is a flow chart illustrating a method of measuring the PPG signal on the optical measurement device of FIG. 21A using feedback from the pressure detection assembly.
Figure 33:
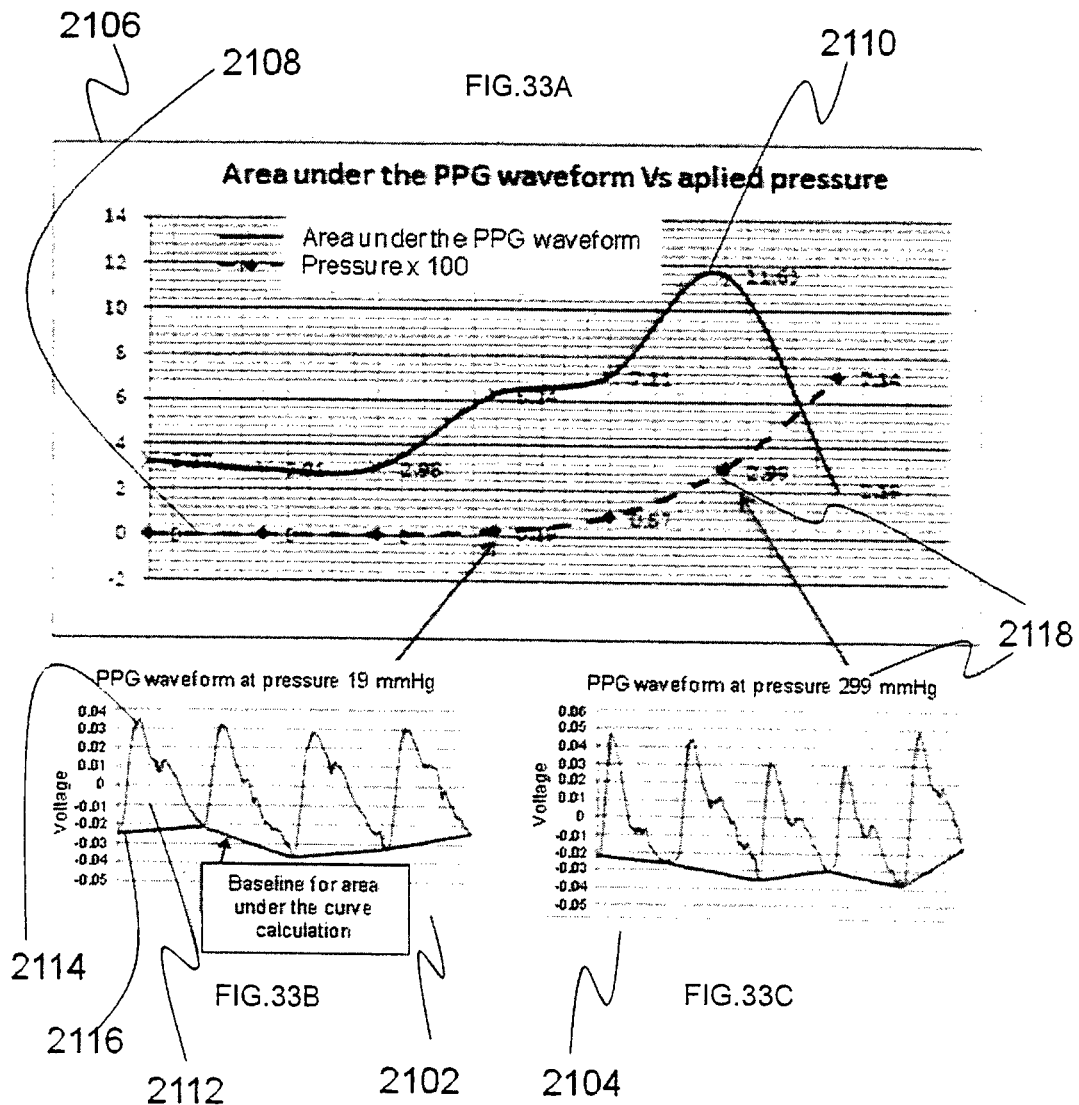
FIGS. 33A, 33B and 33C are graphical representations of the correlation between a PPG waveform and an applied pressure, as would be used in the method of measuring an optimal PPG signal using the optical measurement device of FIG. 21A.

A method of using the optical measurement device 600 is described herein with reference to FIG. 32, with a corresponding exemplary GUI illustrated in FIGS. 33A-33C. A user seeking to obtain his or her PPG signals will first place a body part, such as a finger, on the sensor surface of the optical measurement device (S1402). Calibration of the device to the

TABLE 2

Data Decoding Format

| Time (ms) | Data from Device | DC1 (Hex) | DC2 (Hex) | PPG1 (Hex) | PPG2 (Hex) | FS (Hex) | DC1 (V) | DC2 (V) | PPG1 (V) | PPG2 (V) | FS (V) |
|---|---|---|---|---|---|---|---|---|---|---|---|
| 0 | F0E20A01023A01F00350055E | 0701 | 023A | 01F0 | 0350 | 055E | 2.8905 | 0.9189 | 0.7996 | 1.3671 | 2.2150 |
| 8 | F0E20A01023A02A80347056D | 0701 | 023A | 02A8 | 0347 | 056D | 2.8905 | 0.9189 | 1.0962 | 1.3526 | 2.2392 |
| 16 | F0E20A01023A031802B7057A | 0701 | 023A | 0318 | 02B7 | 057A | 2.8905 | 0.9189 | 1.2768 | 1.1204 | 2.2602 |
| 24 | F0E20A01023A0314026D0584 | 0701 | 023A | 0314 | 026D | 0584 | 2.8905 | 0.9189 | 1.2703 | 1.0011 | 2.2763 |
| 32 | F0E20A01023A029E02D0058C | 0701 | 023A | 029E | 02D0 | 058C | 2.8905 | 0.9189 | 1.0801 | 1.1607 | 2.2892 |
| 40 | F0E20A01023A01E303550591 | 0701 | 023A | 01E3 | 0355 | 0591 | 2.8905 | 0.9189 | 0.7787 | 1.3751 | 2.2973 |
| 48 | F0E20A01023A012D03400592 | 0701 | 023A | 012D | 0340 | 0592 | 2.8905 | 0.9189 | 0.4852 | 1.3413 | 2.2989 |
| 56 | F0E20A01023A00C402AE0591 | 0701 | 023A | 00C4 | 02AE | 0591 | 2.8905 | 0.9189 | 0.3160 | 1.1059 | 2.2973 |
| 64 | F0E20A01023A00D0026E058D | 0701 | 023A | 00D0 | 026E | 058D | 2.8905 | 0.9189 | 0.3353 | 1.0027 | 2.2908 |
| 72 | F0E20A01023A014D02DB0585 | 0701 | 023A | 014D | 02DB | 0585 | 2.8905 | 0.9189 | 0.5368 | 1.1785 | 2.2779 |
| 80 | F0E20A01023A0209035A057B | 0701 | 023A | 0209 | 035A | 057B | 2.8905 | 0.9189 | 0.8399 | 1.3832 | 2.2618 |
| 88 | F0E20A01023A02BC0338056E | 0701 | 023A | 02BC | 0338 | 056E | 2.8905 | 0.9189 | 1.1285 | 1.3284 | 2.2408 |
| 96 | F0E20A01023A031F02A5055F | 0701 | 023A | 031F | 02A5 | 055F | 2.8905 | 0.9189 | 1.2881 | 1.0914 | 2.2167 |
| 104 | F0E20A01023A030B0270054E | 0701 | 023A | 030B | 0270 | 054E | 2.8905 | 0.9189 | 1.2558 | 1.0060 | 2.1893 |
| 112 | F0E20A01023A028802E5053B | 0701 | 023A | 0288 | 02E5 | 053B | 2.8905 | 0.9189 | 1.0447 | 1.1946 | 2.1586 |
| 120 | F0E20A01023A01F00350055E | 0701 | 023A | 01C9 | 035E | 0526 | 2.8905 | 0.9189 | 0.7367 | 1.3896 | 2.1240 |

A raw PPG signal includes DC and AC components, both of which include information critical for waveform analysis. Signal conditioning is therefore performed in order to obtain the information for further processing at the feedback unit. One embodiment of the signal conditioning process will be described below, and may be carried out by components of the illumination and detection assembly 602 illustrated in the block diagram of FIG. 29.

To determine the DC component of the PPG signal, the raw signal 642 obtained from a photodetector 610 is digitized at ADC1 644. The digitized signal will be passed on to both buffer (IR) 646 and buffer (Red) 648 accordingly, which will store up to 100 samples each before sending collated data to the processor 650.

Using the raw samples, a baseline DC component can be determined by the processor 650. At the processor 650, the digital values for Vsub (IR) and Vsub (RED) (i.e. the DC components) are calculated. The Vsub signals 652 are subsequently converted by a digital-to-analog converter (DAC) 654.

The determined DC component (Vsub) is then subtracted from the raw signal, Vraw to obtain Vac 656. The new raw signal, Vac 656, then undergoes a second stage amplification at a second stage amplifier 658 to obtain Vppg 660, where the signal to noise ratio is improved compared with Vraw 642.

Figure 30A:
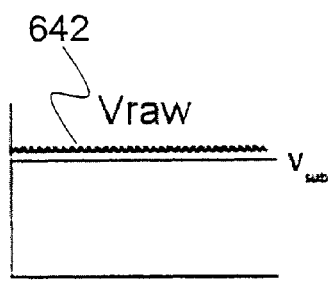
FIGS. 30A, 30B and 30C are graphical illustrations of signals used in the process of obtaining a direct current (DC) component of the PPG signal obtained by the optical measurement device of FIG. 21A.
Figure 30B:
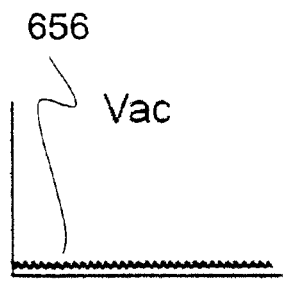
Figure 30C:
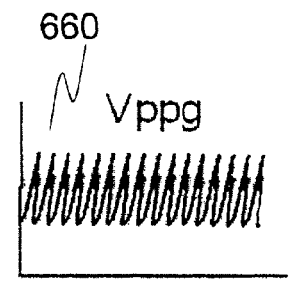

The resolution of the new raw signal 660 is thus enhanced substantially when digitized at ADC2 662, as can be seen from the graphical representations of the Vraw signal 642 in FIG. 30A, Vac 656 in FIG. 30B, and Vppg 660 in FIG. 30C.

Figure 20:
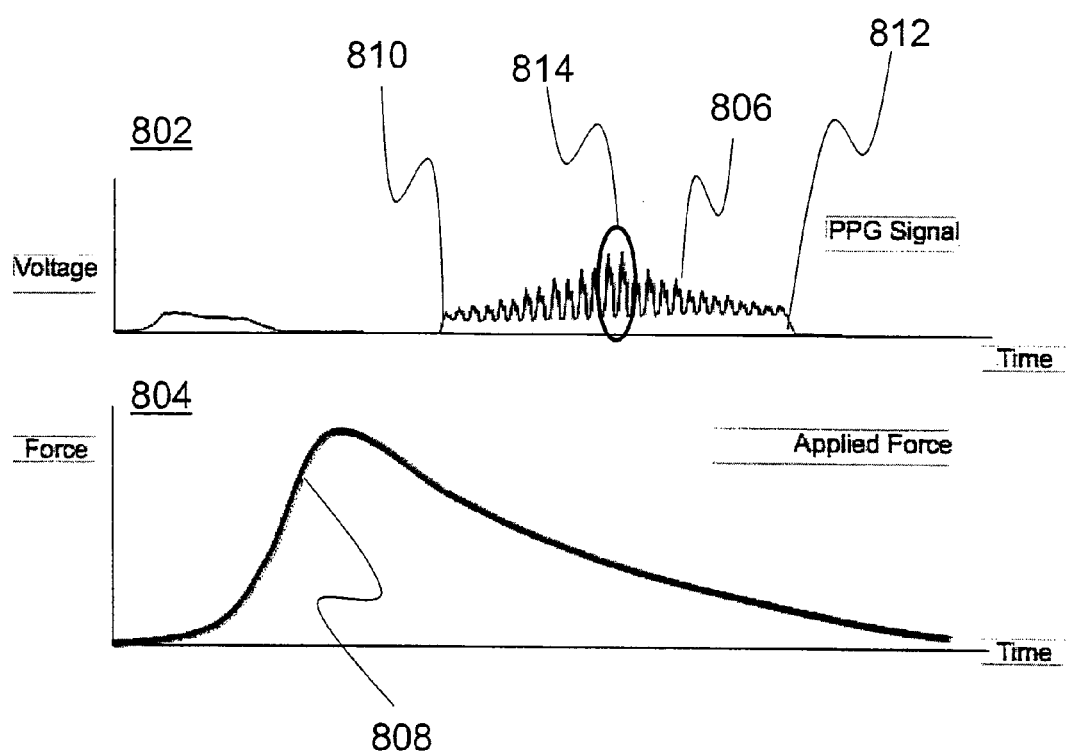
FIG. 20 is a graphical comparison of a graph of measured voltage of a PPG signal over time as it corresponds to a graph of an applied amount of pressure over time.
Figure 31:
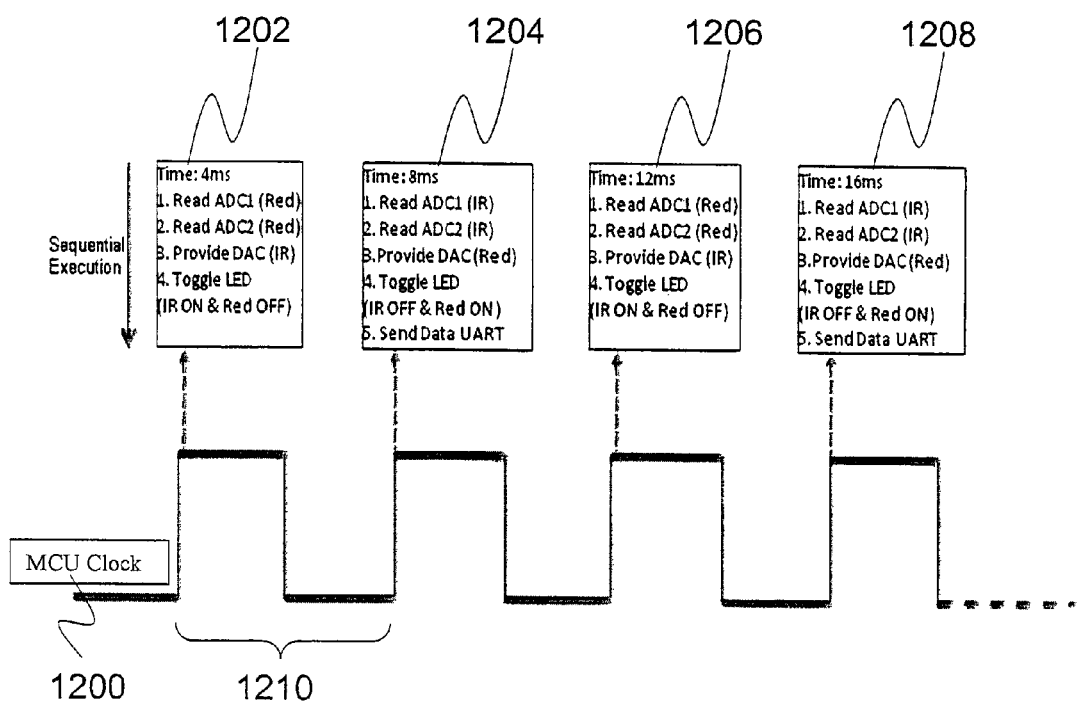
FIG. 31 is an illustration of a sequence of data collection performed during the process of obtaining the PPG signal using the optical measurement device of FIG. 21A.

Referring to FIG. 31, in order to collect the data, an MCU clock 1200 is set to toggle at a predetermined interval to accommodate retrieving results from both LED(IR) and LED (RED) (not shown) during a respective first interval 1202 and second interval 1204. In the non-limiting embodiment shown in FIG. 31, the interval 1210 is set to 4 milliseconds. The data collection sequence is then repeated in the third interval 1206 and fourth interval 1208. Before each toggle between the two LEDs, data from ADC1 644 and ADC2 662 are taken and sent to UART.

individual user may be performed (S1404), where the user is asked to apply an amount of pressure over a specific period of time, corresponding to a force profile 804, (see FIG. 20). In other words, the user is asked to vary the applied pressure such that the system can determine an optimum pressure for the user by analyzing the resulting PPG waveforms that result from the variety of applied pressures (S1406). The user may also be presented with at least one measured PPG waveform generated by a particular amount of applied pressure, as illustrated in the graphical displays in FIGS. 33B and 33C. FIG. 33A is a graphical display 2106 which shows the relationship of a calculated area 2110 under the curve in FIGS. 33B and 33C with respect to applied pressure 2108. FIGS. 33B and 33C are graphical displays 2102 and 2104, respectively, which illustrate the different PPG waveforms at different applied pressures, and how the area under curve of the PPG waveform is computed. As shown in FIG. 33A, the optimum pressure 2118 applied in FIG. 33C, 299 mmHg, corresponds to the largest area 2110 of PPG waveform detected during the calibration (S1404). Once this optimum pressure is determined, a subsequent measurement period begins, during which the user is asked to apply pressure within an optimum range above and below the optimum pressure (S1408). As previously described with regard to FIG. 21A, the amount of pressure being applied by the user may be displayed in a graph 618 on the display 614 so that the user can see the amount of pressure being applied in real-time. The graph 618 may also be displayed using the pressure status bar 620. If the amount of force being applied by the user falls outside of the optimum range, the system can detect this in real-time and will ask the user to increase or decrease the applied pressure in order to remain within the range of optimum pressure and record the best possible PPG signal quality (S1410).

Optimum pressure is determined as the pressure at which the measured PPG signal has the largest waveform amplitude, or area 2112 under the PPG waveform, as shown in FIG. 33B by the area 2112 bounded by the PPG signal 2114 and baseline 2116. FIG. 33A then graphs the variation of the area 2112 under the PPG waveform with respect to the pressure 2108 applied on the sensor. As may be observed in this example, the optimum pressure 2118 is at 299 mmHg, where area 2112 under the curve is at its maximum of 11.63.

Figure 34:
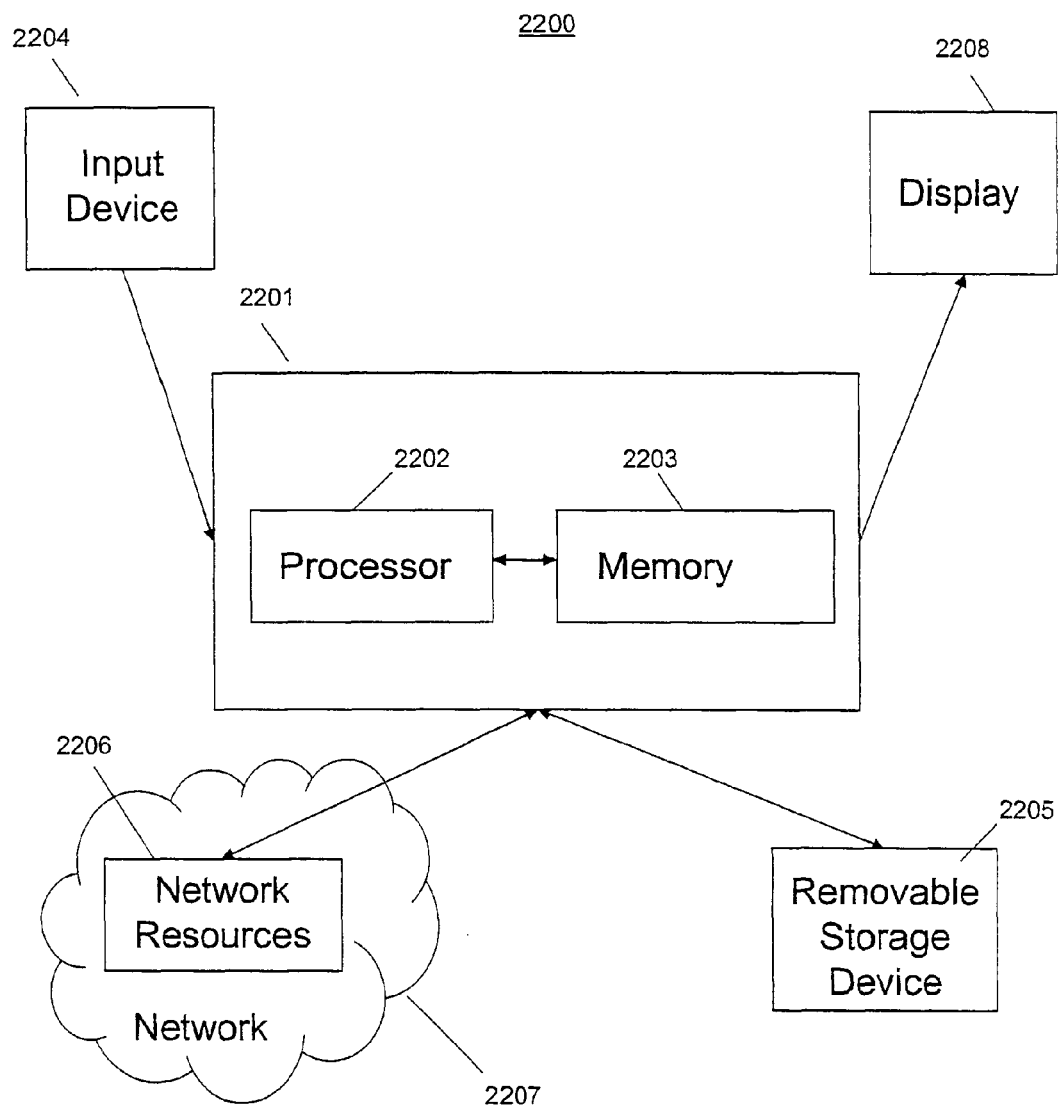
FIG. 34 is a block diagram of a computer system upon which the device and methods may be implemented, according to an exemplary embodiment.

FIG. 34 is a block diagram that illustrates an embodiment of a computer/server system 2200 as the feedback unit 606 upon which an embodiment of the inventive methodology may be implemented. The system 2200 includes a computer/server platform 2201 including a processor 2202 and memory 2203 which operate to execute instructions, as known to one of skill in the art. The term "computer-readable medium" as used herein refers to any medium that participates in providing instructions to processor 2202 for execution. Additionally, the computer platform 2201 receives input from a plurality of input devices 2204, such as a keyboard, mouse, touch device or verbal command. The computer platform 2201 may additionally be connected to a removable storage device 2205, such as a portable hard drive, optical media (CD or DVD), disk media or any other medium from which a computer can read executable code. The computer platform may further be connected to network resources 2206 which connect to the Internet or other components of a local public or private network. The network resources 2206 may provide instructions and data to the computer platform from a remote location on a network 2207. The connections to the network resources 2206 may be via wireless protocols, such as the 802.11 standards, Bluetooth® or cellular protocols, or via physical transmission media, such as cables or fiber optics. The network resources may include storage devices for storing data and executable instructions at a location separate from the computer platform 2201. The computer interacts with a display 2208 to output data and other information to a user, as well as to request additional instructions and input from the user. The display 2208 may therefore further act as an input device 2204 for interacting with a user.

The monitoring of (i) the PPG signal from the illumination and detection assembly and (ii) the amount of force exerted by an individual from the pressure assembly thus enables the optical measurement device to obtain an optimum PPG signal with a high signal to noise ratio. The signal to noise ratio is augmented in an optical signal. The optical measurement device provides for a PPG signal to be acquired at a zero transmural pressure that is unique to each user using the device.

It should be appreciated that the embodiment described herein aims to provide a device and method capable of augmenting signal to noise ratio in an optical signal of an illuminated region at a measuring site of a body part of a user. The embodiment also provides for detecting the optical response formed by both light reflected from the measuring site and the light transmitted through the measuring site. The embodiment described herein utilize redirecting reflections of light on its way towards the measuring site (i.e. blood vessels) back to the region of interest.

In an additional exemplary embodiment, the device may perform a series of calibration steps for each individual user in order to determine an optimum range of pressure for each individual. The subsequent steps of capturing the PPG signal will then use the predetermined optimum range as the benchmark for obtaining an optimum PPG signal. The described embodiment is not to be construed as imitative. For example, the described embodiment describes the use of three parameters RR, SpO2 and HR but the combination of SpO2 and one other parameter (RR or HR) is envisaged. Also, more parameters (e.g. physiological signals from the user) might be added to increase the accuracy of the health indication.

In the described embodiment, reference is made to a "user" or human subject but it should be appreciated that the embodiment may be adapted to apply to other subjects such as animals.

The reference scoring system is illustrated as a chart in FIG. 9 but the system may take other forms, especially if the method is implemented by a computer. In other words, the described method need not be implemented by a computer and may be implemented by manual means.

Figure 23:
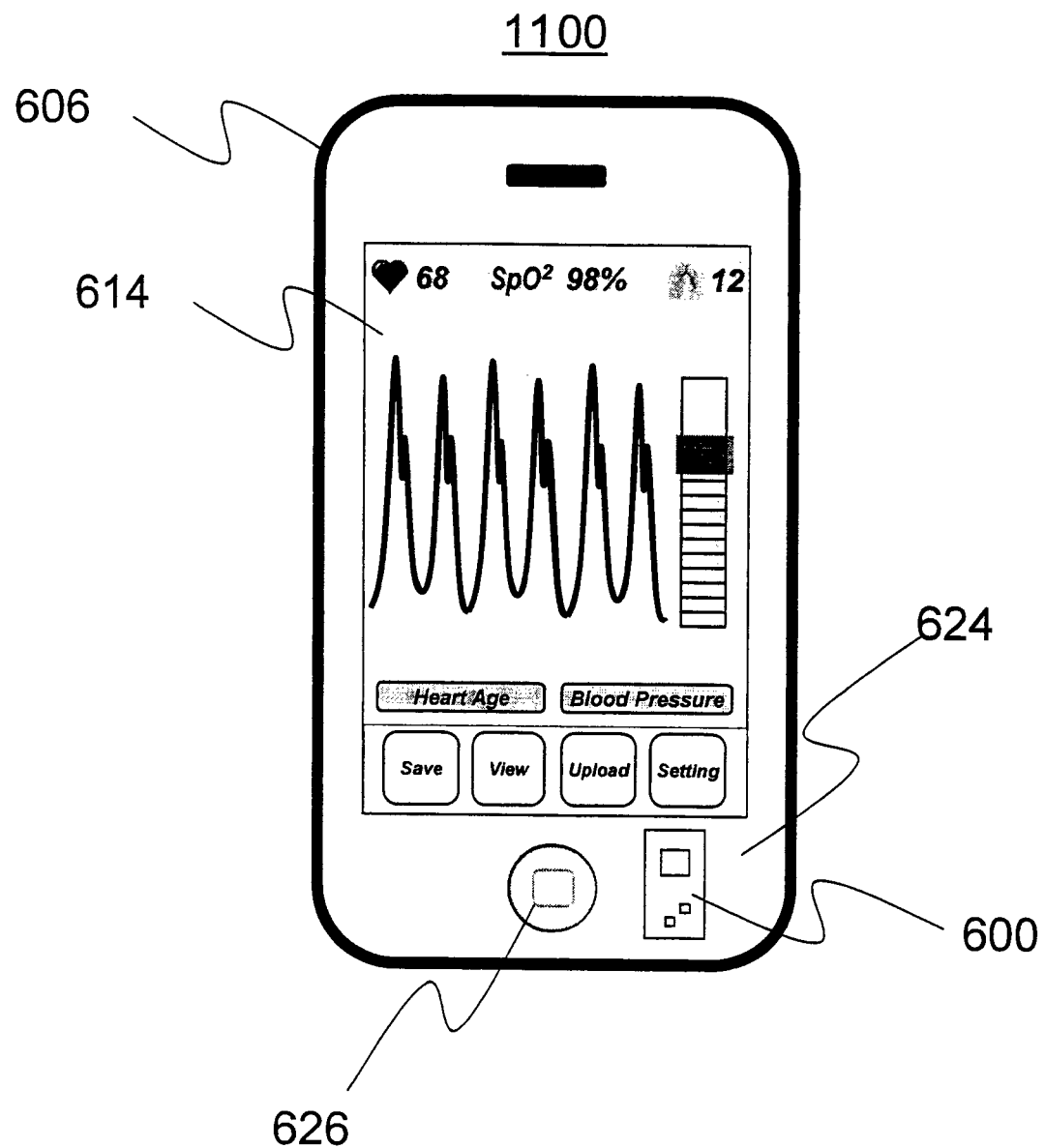
FIG. 23 illustrates a portable device integrated with an optical measurement device, which is a variation of the feedback unit of FIG. 21A/21B.
Figure 29:
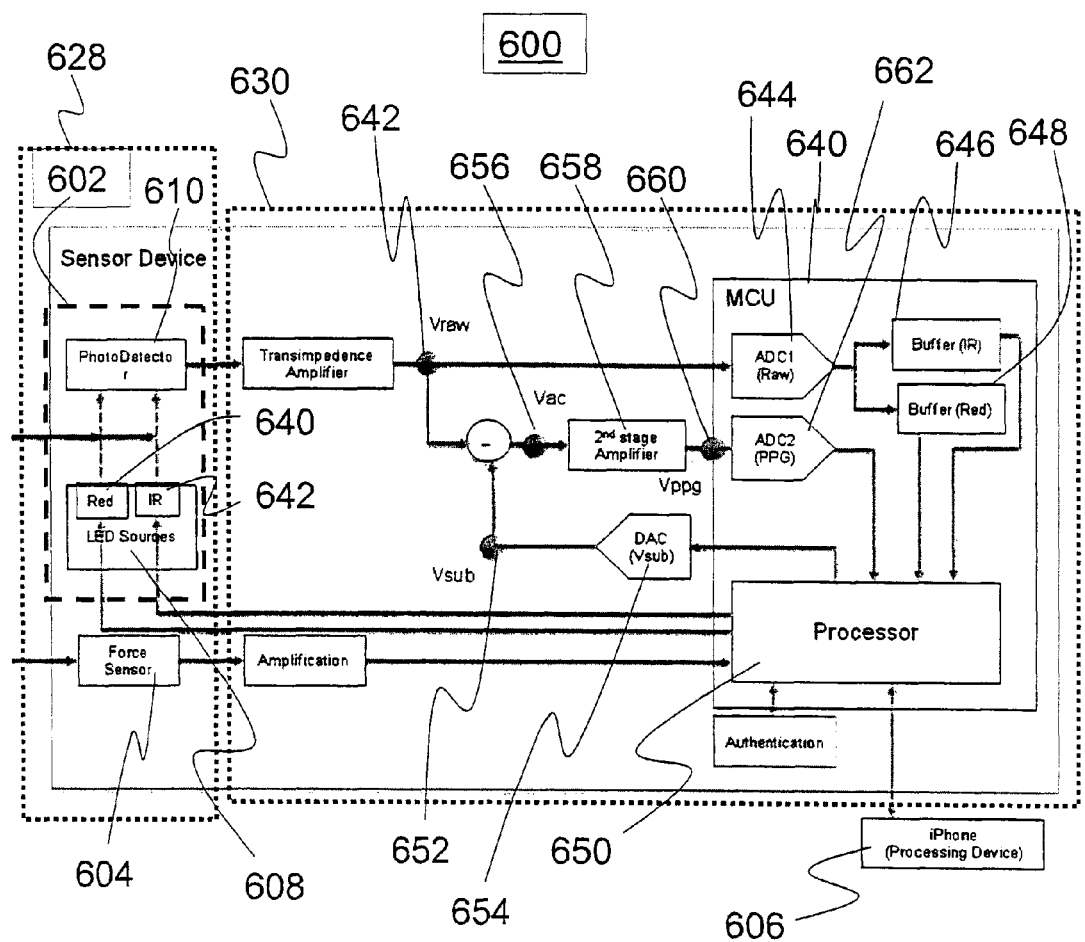
FIG. 29 is a block diagram of the optical measurement device of FIG. 21A/21B.

In the described embodiment, the optical measurement device 600 is separate from the feedback unit 606 but this may not be so. For example, a portable device may be integrated with the optical detection device as a single optical measurement device 1100, as shown in FIG. 23. The optical detection device 600 is incorporated within a housing 624 of a portable device 606; in this case located near a menu button 626 of the portable device 606 and separate from a display 614. With such a configuration, the portable device 606 is capable of carrying out processing functions for the optical detection device 600, such as signal conditioning and signal processing. As described below with regard to the block diagram in FIG. 29, the optical detection device 600 integrated with the portable device 606 would only require a sensing portion 628, while a processing portion 630 would be provided by hardware and firmware of the of the portable device 606. The sensing portion 628 would include the illumination and detection assembly 602 and the pressure detection assembly 604, as illustrated in FIG. 29.

Figure 24:
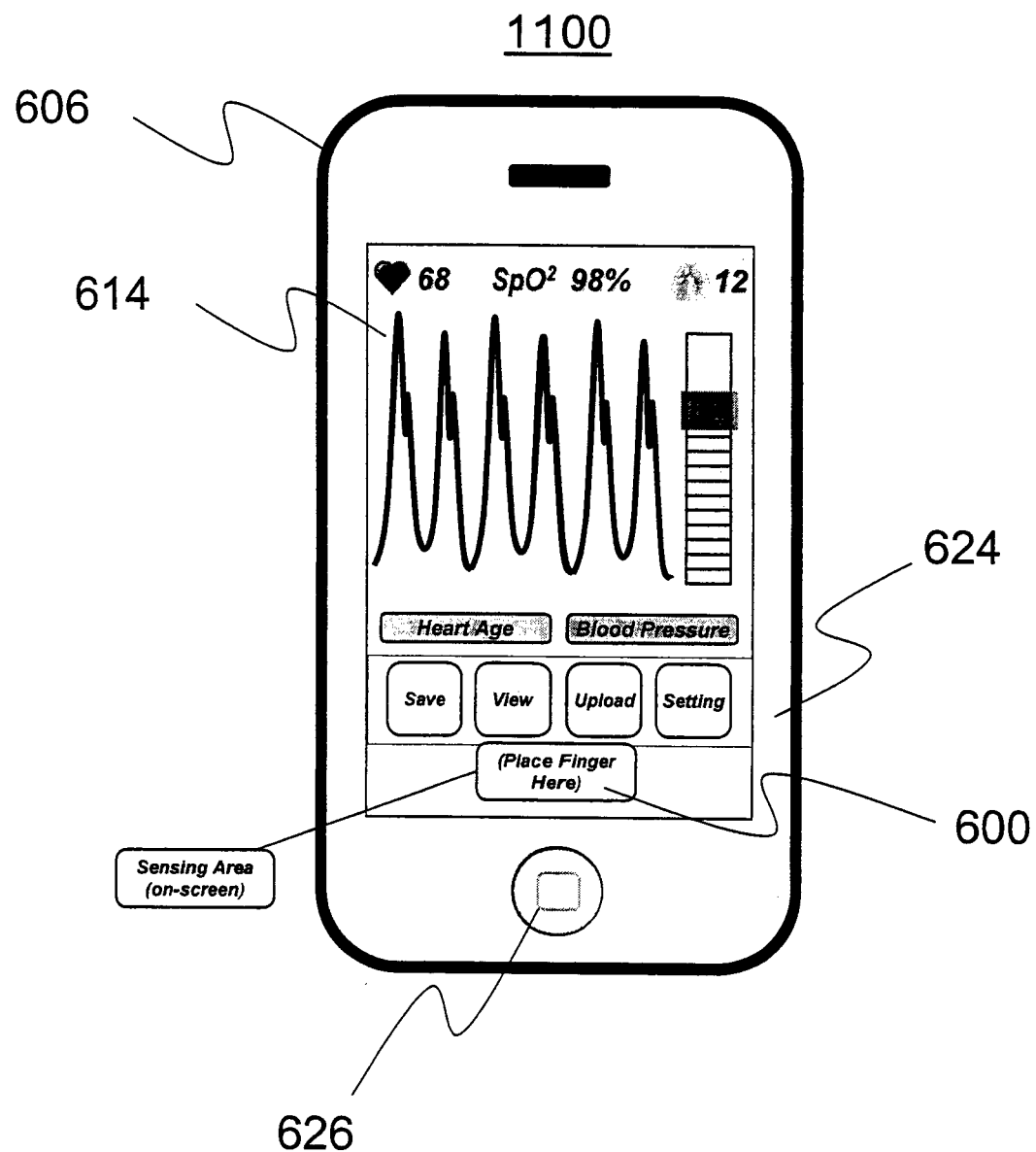
FIG. 24 illustrates an optical measurement device integrated with a touch screen display of a portable device, which is a further variation of the feedback unit of FIG. 21A/21B.

In another exemplary embodiment illustrated in FIG. 24, the optical detection device 600 may be integrated with the display 614 when the display is a touch screen display. Two openings may be created in the touch screen display to permit the transmission of light from the LED light sources and to the photodetector. The components of the touch screen display 614 would have accurate pressure-sensing capabilities to detect the amount of pressure applied on the touch screen display 614, such that the functions of the pressure detection assembly can be provided by the touch screen display 614 directly, thereby eliminating the need for a separate pressure detection assembly.

Therefore, only the illumination and detection assembly of the optical detection device would be separately required, such as red and infrared (IR) LED light sources and a photodetector.

In another exemplary embodiment, the illumination and detection assembly may comprise a camera and flash of a smartphone or other portable device, such that the camera functions as the photodetector while the flash functions as the light source. The flash and camera would be located proximate to each other on the portable device, and the flash would be configured with a red LED and infrared LED to output the required wavelengths of light. In this exemplary embodiment, the pressure detection assembly would be the only significant modification required on the portable device.

Figure 25A:
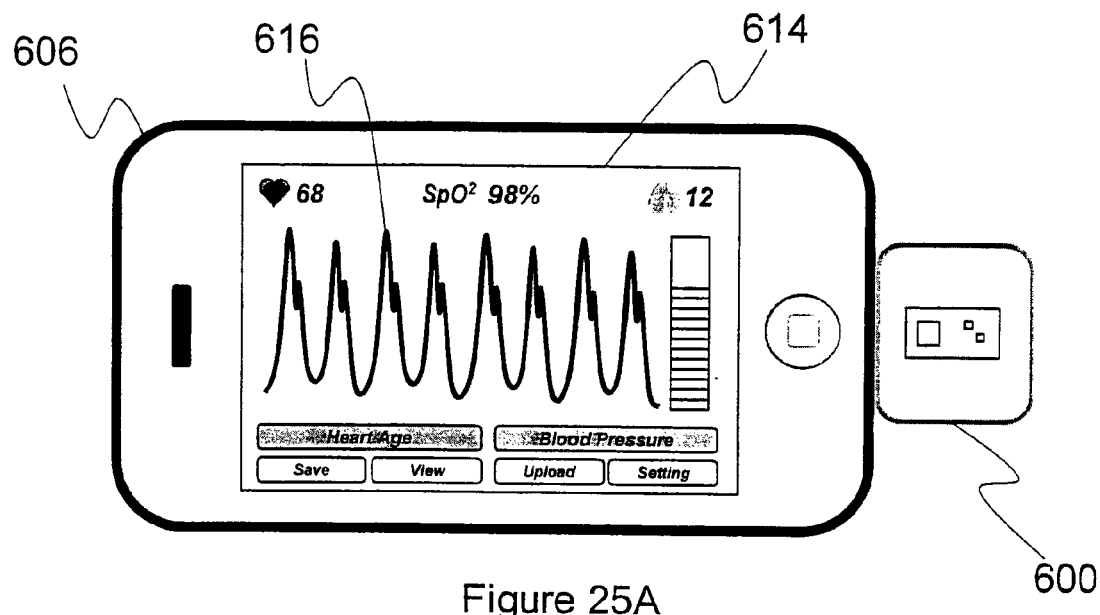
FIGS. 25A and 25B illustrate a portable device connected with an optical measurement device configured in a landscape orientation and a user's interaction therewith respectively, which is yet a further variation of the feedback unit of FIG. 21A/21B.
Figure 25B:
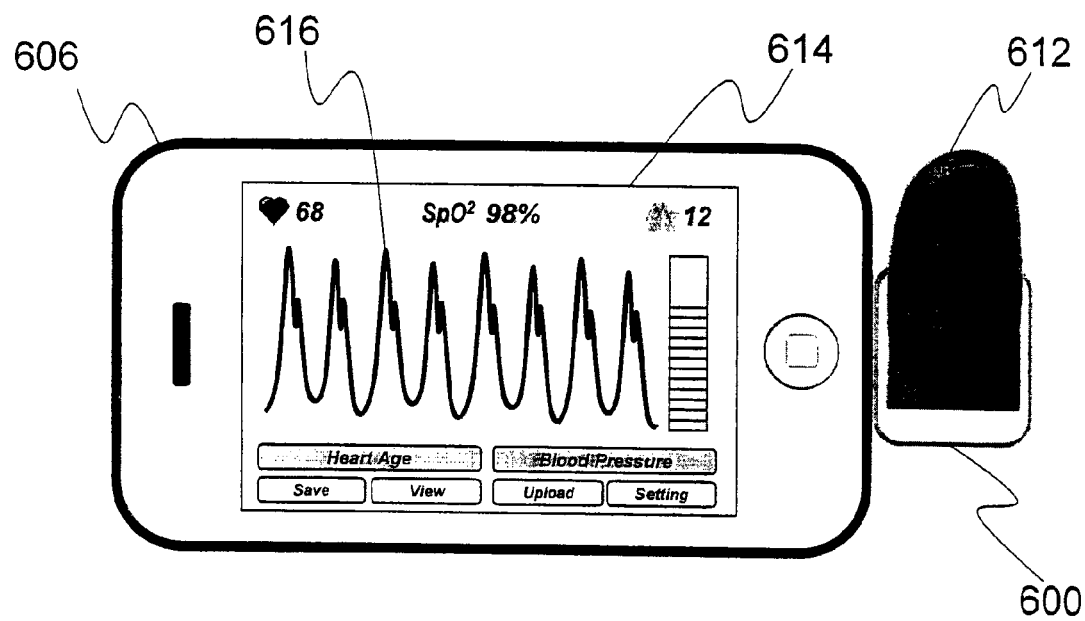

FIGS. 25A and 25B illustrate yet another exemplary embodiment, where the portable device 606 may be oriented in a landscape configuration such that the user views the display 614 horizontally and interacts with the optical detection device 600 in a way that is easier for the user to hold the portable device 606 in the user's hands. In landscape orientation, the user can place a finger 612 on the optical detection device 600 and more easily view a larger time period of the PPG signal 616.

Figure 26A:
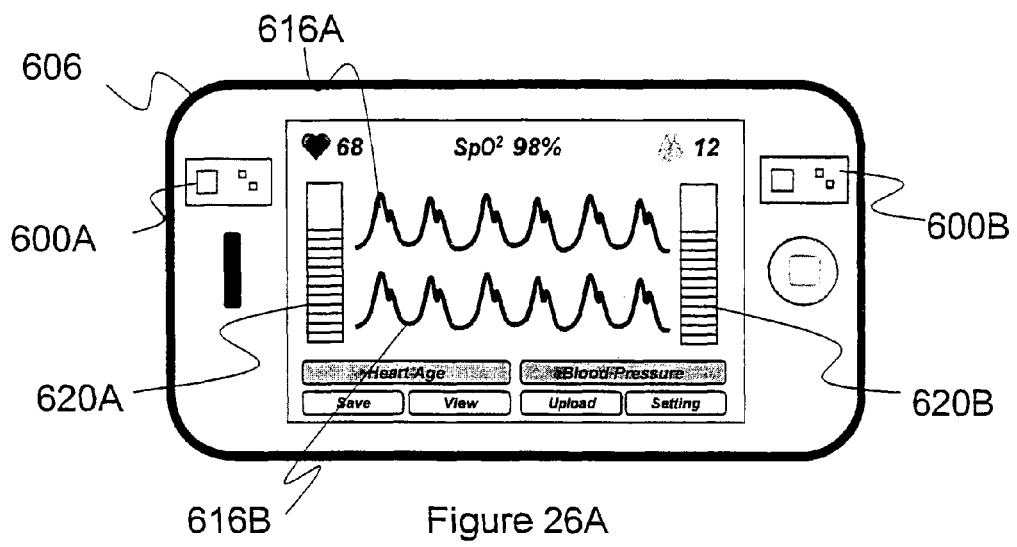
FIGS. 26A and 26B illustrate a portable device integrated with a plurality of optical measurement devices in a landscape orientation and a user's interaction therewith respectively, which is an even further variation of the feedback unit of FIG. 21A/21B.
Figure 26B:
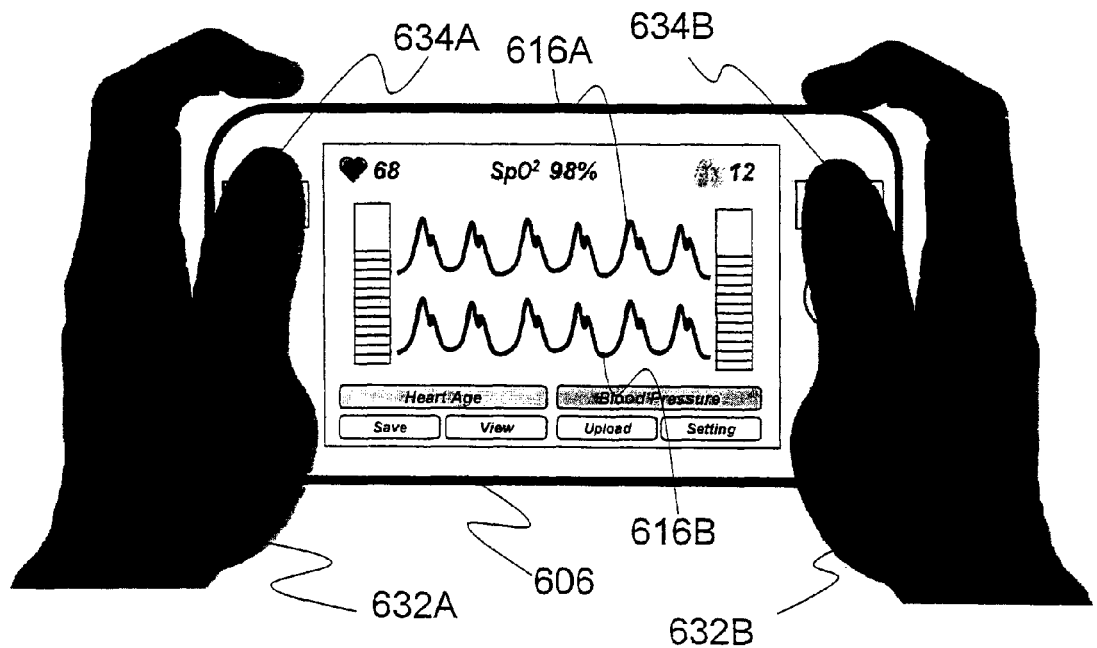
Figures 27A, 27B:
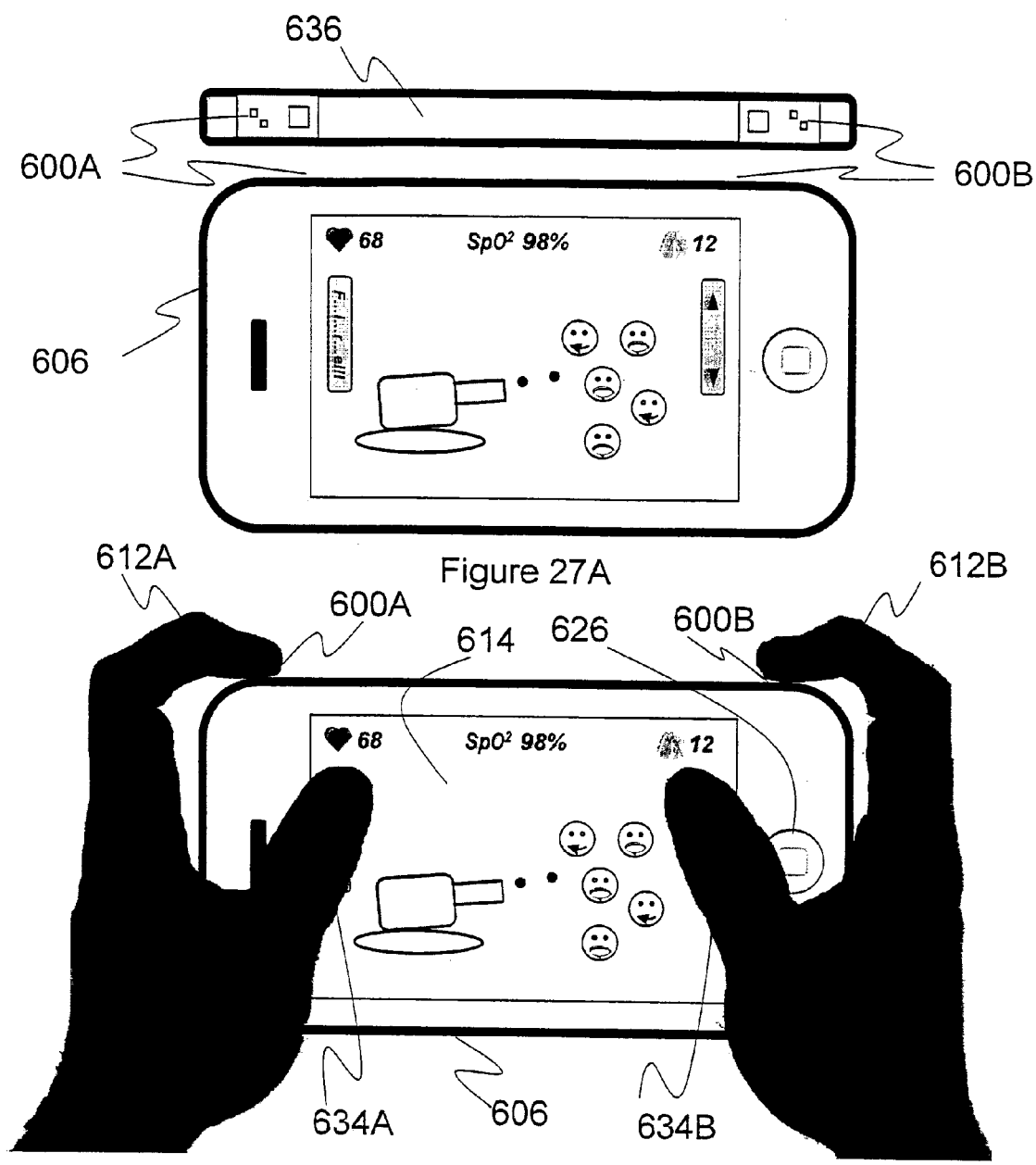
FIGS. 27A and 27B illustrate a portable device integrated with a plurality of optical measurement devices located on a side portion of the portable device, which are variations of the feedback unit of FIG. 21A/21B.

FIGS. 26A and 26B illustrate another exemplary embodiment, where a plurality of optical detection devices 600A and 600B are integrated with the portable device 606 for interaction with the user in a landscape orientation. The use of more than one optical detection device will allow measurement of additional physiological properties. As shown in FIG. 26B, the user can easily hold the portable device 606 with both hands 632A and 632B while also placing their thumbs 634A and 634B on the corresponding optical detection devices 600A and 600B. In a similar exemplary embodiment illustrated in FIGS. 27A and 27B, the optical detection devices 600A and 600B may be located on a side portion 636 of the portable device 606, so that the user can place index fingers 612A and 612B in contact with the corresponding optical detection devices 600A and 600B in a natural configuration. In this embodiment, the user's thumbs 634A and 634B are then free to operate the portable device by interacting with the touch screen display 614 or menu button 626 while the index fingers are being sensed by the optical detection devices 600A and 600B. In the embodiments illustrated in FIGS. 26A/26B and 27A/27B, because there are a plurality of optical detection devices 600A and 600B, there may also be a corresponding plurality of PPG signals 616A and 616B and pressure status bars 620A and 620B accordingly.

The feedback unit may also include software or other computer programmable instructions which carry out instructions relating to receiving and processing the PPG signal, the pressure measurements, and creation of the output to the user relating to the correlation of the detected PPG signal and pressure measurements.

Figure 28A:
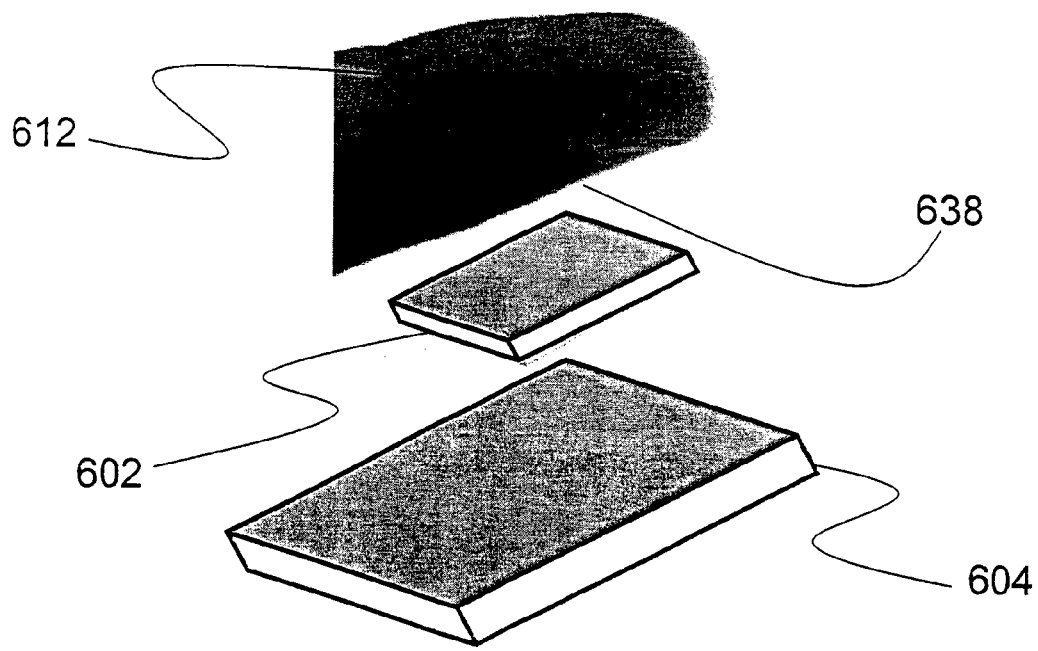
FIGS. 28A and 28B are expanded view illustrations of an alternate embodiment of a method of using the optical measurement device with the human finger to detect the blood pressure of the human, according to one exemplary embodiment.
Figure 28B:
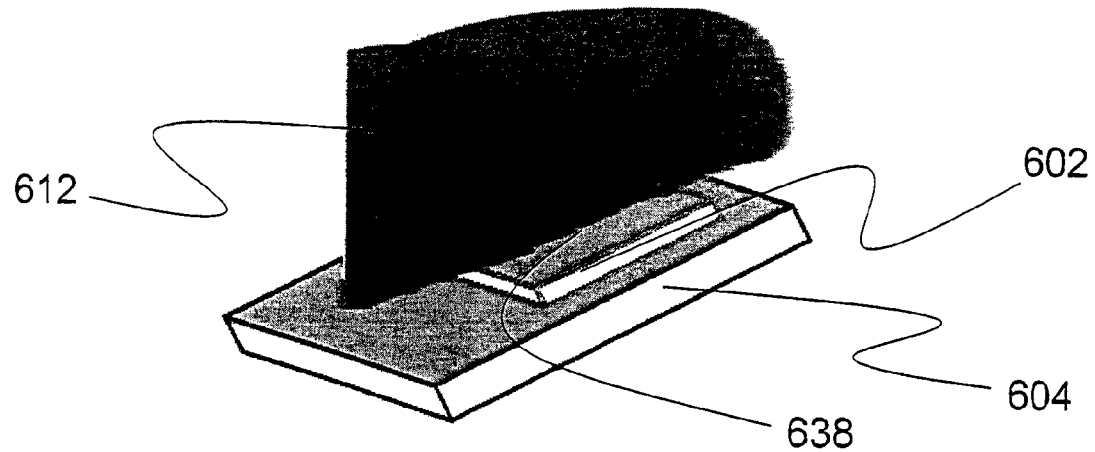

As described herein, the resulting optimal PPG signal provides a highly accurate measurement of various physiological parameters detected by photoplethysmography, such as a saturation level of oxygen in blood (i.e. SpO2). However, other parameters may be obtained and us in the derivation of the health index. For example, the optical measurement device may further include acquisition of systolic and diastolic blood pressure parameters. One option for detecting the parameters to determine blood pressure involves placing the side 638 of the finger 612 where the digital artery lies onto the illumination and detection assembly 602, as illustrated in FIGS. 28A and 28A. As shown in FIG. 20, a PPG signal 806 in the PPG signal graph 802 is monitored while the user applies vertical downward force onto the pressure sensor 604 following a pre-determined applied force profile 808 with respect to time, as shown in the applied pressure graph 804. The basic fundamental behind this analysis is to identify when the PPG signal 806 begins to display a PPG waveform (point 810) and when the PPG signal finally dies off (point 812), as these points are indirectly associated with the highest and lowest point of the blood pressure. In addition, with this analysis, the external pressure needed to achieve zero transmural pressure can be determined. When zero transmural pressure is achieved, the PPG waveform reflects the highest amplitude, as shown at area 814 in the PPG signal graph 802. In FIG. 20, as the amount of applied pressure follows the profile 808 of rapid increase and gradual decrease over time, the PPG waveform 806 changes in amplitude accordingly. Thus, looking at the entire range of PPG waveform from 810 to 812 with respect to applied force 808, the highest amplitude PPG waveform 814 provides an indication of the corresponding position on the applied pressure graph 804 where an amount of applied pressure results in zero transmural pressure state.

Having now fully described the invention, it should be apparent to one of ordinary skill in the art that many modifications can be made hereto without departing from the scope as claimed.

The invention claimed is:

1. A computer implemented method of deriving a health index for determining cardiovascular health of a subject; the method performed by a computing device and comprising
    (i) obtaining values of at least two parameters from one or more PPG signals of the subject, the at least two parameters including Sp02 and at least one other parameter related to Sp02;
    (ii) assigning, using the computing device, a score using the values of the at least two related parameters from a reference scoring system, wherein the reference scoring system is derived, using the computing device, by
        listing all possible permutations of the at least two parameters in a list, each permutation corresponding to a preliminary band classification and a preliminary score;
        checking the list against a list of impossible combinations and atypical combinations;
        identifying, using the computing device, which of the possible permutations in the list falls within the list of impossible combinations and atypical combinations and marking the identified possible permutations;
        manipulating, using the computing device, the preliminary band classification of the possible permutations identified as atypical combinations;
        manipulating, using the computing device, the preliminary scores corresponding to the manipulated preliminary band classifications based on predefined scores and band classification relationships;
        deriving, using the computing device, a plurality of groupings for each parameter from the list of possible permutations and the manipulated scores and band classifications; each grouping including a range of readings for the respective parameter and is associated with a corresponding score for assigning to, and dependence on, the obtained values; and
    (iii) deriving, using the computing device, the health index based on the assigned score; wherein the health index is derived by deriving a preliminary health index from the groupings for each parameter based on the obtained values and verifying if a combination of the groupings is medically possible, and further verifying if the preliminary health index requires corrective adjustment based on the combination of the groupings.

2. A computer implemented method according to claim 1, wherein the at least one other parameter is selected from the group consisting of heart rate and respiratory rate.

3. A computer implemented method according to claim 1, wherein the score is assigned from a combination of the values of the at least two parameters.

4. A computer implemented method according to claim 1, each corresponding score is associated with clinical interpretation of the cardiovascular health of the subject.

5. A computer implemented method according to claim 1, further comprising adding, using the computing device, the assigned scores together to derive the health index to represent the cardiovascular health of the subject.

6. A computer implemented method according to claim 1, further comprising adding up, using the computing device, the assigned scores to derive the preliminary health index.

7. A computer implemented method according to claim 1, wherein if the combination of the groupings is medically not possible, displaying an error message, using the computing device, as the health index.

8. A computer implemented method according to claim 1, wherein if adjustment is needed, adjusting, using the computing device, the preliminary health index to a revised health index and using the revised health index as the health index.

9. A computer implemented method according to claim 1, wherein verifying if the preliminary health index requires adjustment includes comparing, using the computing device, the combination of groupings with a reference list of combinations.

10. A computer implemented method according to claim 1, wherein the at least one other parameter is categorized based on the subject's age group and gender.

11. A computer implemented method according to claim 1, wherein the health index is associated with clinical interpretation of the cardiovascular health of the subject, and the method further includes displaying, using the said computing device, the clinical interpretation as part of the health index.

12. A computer implemented method according to claim 1, wherein the at least two parameters are obtained from more than one PPG signals.

13. A computer implemented method according to claim 1, wherein the score is based on relative health significance of the parameters considered collectively.

14. A computer implemented method according to claim 1, wherein (i) further includes:
   illuminating a portion of living tissue of the subject and detecting transmitted or reflected light as a signal using an illumination and detection assembly;
   detecting an amount of pressure applied by the portion of living tissue of the subject to the illumination and detection assembly;
   correlating the quality of the detected signal with the amount of applied pressure; and
   providing feedback related to the correlation to the subject.

15. A computer implemented method according to claim 14, further comprising providing an indication, using the computing device, of whether the amount of pressure being applied to the illumination and detection assembly should be adjusted.

16. A computer implemented method according to claim 14, further comprising displaying, using the computing device, a range of optimal applied pressures along with actual applies pressure being applied by the subject.

17. A computer implemented method according to claim 14, further comprising displaying, using the computing device, a range of optimal applied pressures which corresponds to a state of zero transmural pressure.

18. A computer implemented method according to claim 14, wherein the PPG signal is obtained when the applied pressure is at its optimal.

19. Apparatus for deriving a health index for determining cardiovascular health of a subject, the apparatus comprising
   a processor configured to
   (i) obtain values of at least two parameters from a PPG signal of the subject, the at least two parameters including Sp02 and at least one other parameter related to Sp02;
   (ii) assign a score using the values of the at least two parameters from a reference scoring system, wherein the reference scoring system is derived by
      listing all possible permutations of the at least two parameters in a list, each permutation corresponding to a preliminary band classification and a preliminary score;
      checking the list against a list of impossible combinations and atypical combinations;
      identifying which of the possible permutations in the list falls within the list of impossible combinations and atypical combinations and marking the identified possible permutations;
      manipulating the preliminary band classification of the possible permutations identified as atypical combinations;
      manipulating the preliminary scores corresponding to the manipulated preliminary band classifications based on predefined scores and band classification relationships;
      deriving a plurality of groupings for each parameter from the list of possible permutations and the manipulated scores and band classifications; each grouping including a range of readings for the respective parameter and is associated with a corresponding score for assigning to, and dependence on, the obtained values; and
   (iii) derive the health index based on the assigned scores, wherein the health index is derived by deriving a preliminary health index from the groupings for each parameter based on the obtained values; and wherein the processor is configured to verify if a combination of the groupings is medically possible, and to further verify if the preliminary health index requires corrective adjustment based on the combination of the groupings.

20. An apparatus according to claim 19, wherein the apparatus is in the form of a mobile phone.

* * * * *